United States Patent [19]

Atkinson et al.

[11] Patent Number: 5,484,409
[45] Date of Patent: Jan. 16, 1996

[54] INTRAVASCULAR CATHETER AND METHOD FOR USE THEREOF

[75] Inventors: Robert Atkinson, New Brighton; Peter Keith, Fridley; Louis G. Ellis, St. Anthony; Dale Schmaltz, St. Paul; David Robinson, Channassen, all of Minn.

[73] Assignee: SciMed Life Systems, Inc., Maple Grove, Minn.

[21] Appl. No.: 23,950

[22] Filed: Feb. 26, 1993

Related U.S. Application Data

[63] Continuation-in-part of Ser. No. 843,647, Feb. 28, 1992, which is a continuation-in-part of Ser. No. 830,479, Feb. 4, 1992, which is a continuation of Ser. No. 398,756, Aug. 25, 1989, abandoned.

[51] Int. Cl.$^6$ .......................... A61M 5/00; A61M 29/00
[52] U.S. Cl. .............................. 604/96; 606/191
[58] Field of Search ............... 604/96–98, 122, 604/118–119, 192–194, 236; 606/191–192

[56] References Cited

U.S. PATENT DOCUMENTS

| | | |
|---|---|---|
| 3,890,977 | 6/1975 | Wilson . |
| 4,194,513 | 3/1980 | Rhine et al. . |
| 4,425,919 | 1/1984 | Alston, Jr. et al. . |
| 4,445,892 | 5/1984 | Hussein et al. ................ 604/101 |
| 4,554,929 | 11/1985 | Samson et al. . |
| 4,573,470 | 3/1986 | Samson et al. . |
| 4,616,653 | 10/1986 | Samson et al. . |
| 4,641,654 | 2/1987 | Samson et al. . |
| 4,646,742 | 3/1987 | Packard et al. . |
| 4,654,025 | 3/1987 | Cassou et al. . |
| 4,723,550 | 2/1988 | Bales et al. ................ 604/154 |
| 4,762,129 | 8/1988 | Bonzel ................ 606/194 |
| 4,817,613 | 4/1989 | Jaraczewski et al. . |
| 4,838,268 | 6/1989 | Keith et al. . |
| 4,846,174 | 7/1989 | Willard et al. . |
| 4,846,193 | 7/1989 | Tremulis et al. . |
| 4,848,344 | 7/1989 | Sos et al. . |
| 4,892,519 | 1/1990 | Songer et al. . |
| 4,898,577 | 2/1990 | Badger et al. . |
| 4,906,241 | 3/1990 | Noddin et al. . |
| 4,928,693 | 5/1990 | Goodin et al. . |
| 4,932,413 | 6/1990 | Shockey et al. . |
| 4,964,409 | 10/1990 | Tremulis ................ 606/191 |
| 4,967,753 | 11/1990 | Haase et al. . |
| 4,976,720 | 12/1990 | Machold et al. . |
| 4,986,814 | 1/1991 | Burney et al. . |
| 4,988,356 | 1/1991 | Crittenden et al. . |

(List continued on next page.)

FOREIGN PATENT DOCUMENTS

| | | |
|---|---|---|
| 10067/88 | 6/1988 | Australia . |
| 0513818A1 | 11/1992 | European Pat. Off. . |
| WO92/00775 | 1/1992 | WIPO . |
| WO94/11047 | 5/1994 | WIPO . |

*Primary Examiner*—Stephen C. Pellegrino
*Assistant Examiner*—Nancy Mulcare
*Attorney, Agent, or Firm*—Nawrocki, Rooney & Sivertson

[57] ABSTRACT

An intravascular catheter, such as a balloon catheter, and a method for use thereof, the catheter comprising an elongate shaft having an inflation lumen extending therethrough, an implement, such as a dilation balloon, connected to and located at the distal portion of the shaft and communicating with the lumen, a small profile core wire extending through at least the dilation balloon and having a distal portion that extends distally from the dilation balloon through a distal core wire opening located distally of the balloon, and further in which the core wire is movable relative to the elongate shaft to allow withdrawal of the elongate shaft and the balloon while leaving the core wire positioned intravascularly, and a tip member connected to the core wire in a region thereof distal of the location at which the core wire extends distally of the core wire opening, the tip member having a profile larger than the opening. Also, a manifold is provided adapted to both form a fluid seal around a guide wire received in a port and spatially fix the position of the guide wire in the manifold. Also, the manifold automatically closes a fluid port upon disconnection of a source of fluid from the fluid port.

22 Claims, 7 Drawing Sheets

U.S. PATENT DOCUMENTS

| | | |
|---|---|---|
| 4,994,027 | 2/1991 | Farrell . |
| 4,998,917 | 3/1991 | Gaiser et al. . |
| 5,003,990 | 4/1991 | Osypka . |
| 5,007,901 | 4/1991 | Shields . |
| 5,015,231 | 5/1991 | Keith et al. . |
| 5,026,607 | 6/1991 | Kiezulas . |
| 5,031,636 | 7/1991 | Gambale et al. . |
| 5,032,113 | 7/1991 | Burns . |
| 5,045,061 | 9/1991 | Seifert et al. . |
| 5,046,497 | 9/1991 | Millar . |
| 5,047,018 | 9/1991 | Gay et al. . |
| 5,047,045 | 9/1991 | Arney et al. . |
| 5,057,092 | 10/1991 | Webster, Jr. . |
| 5,066,285 | 11/1991 | Hillstead . |
| 5,114,403 | 5/1992 | Clarke et al. . |
| 5,120,308 | 6/1992 | Hess . |
| 5,125,905 | 6/1992 | Wright et al. . |
| 5,171,221 | 12/1992 | Samson . |
| 5,171,298 | 12/1992 | Walker et al. . |
| 5,209,728 | 5/1993 | Kraus et al. . |
| 5,217,434 | 6/1993 | Arney .................. 604/99 |
| 5,221,260 | 6/1993 | Burns et al. ............ 604/99 |
| 5,250,034 | 10/1993 | Appling et al. . |
| 5,256,144 | 10/1993 | Kraus et al. ............ 604/96 |
| 5,259,839 | 11/1993 | Burns ................... 604/99 |
| 5,265,622 | 11/1993 | Barbere . |
| 5,290,247 | 3/1994 | Crittenden . |
| 5,304,198 | 4/1994 | Samson ................. 606/194 |
| 5,305,740 | 4/1994 | Kolobow . |
| 5,312,340 | 5/1994 | Keith . |
| 5,318,529 | 6/1994 | Kontos . |
| 5,320,604 | 6/1994 | Walker et al. ........... 604/96 |
| 5,324,259 | 6/1994 | Taylor et al. ........... 604/96 |
| 5,348,537 | 9/1994 | Wiesner et al. ......... 604/96 |
| 5,364,354 | 11/1994 | Walker et al. ........... 604/96 |

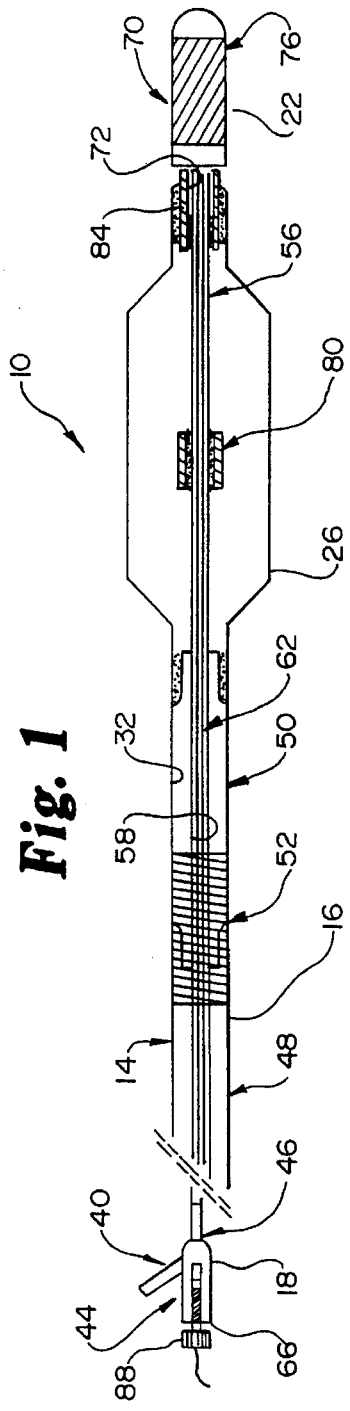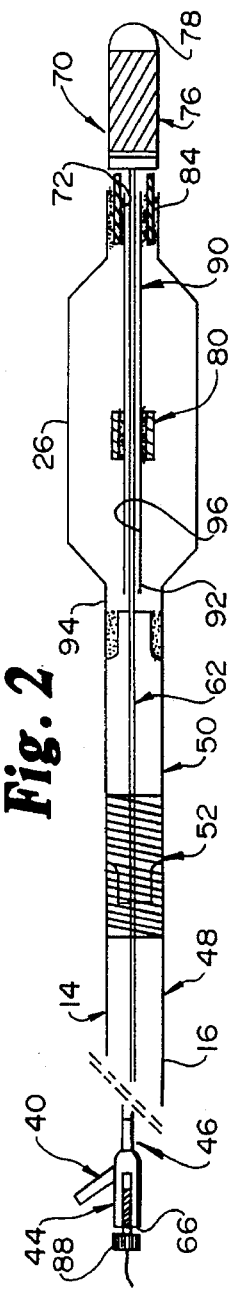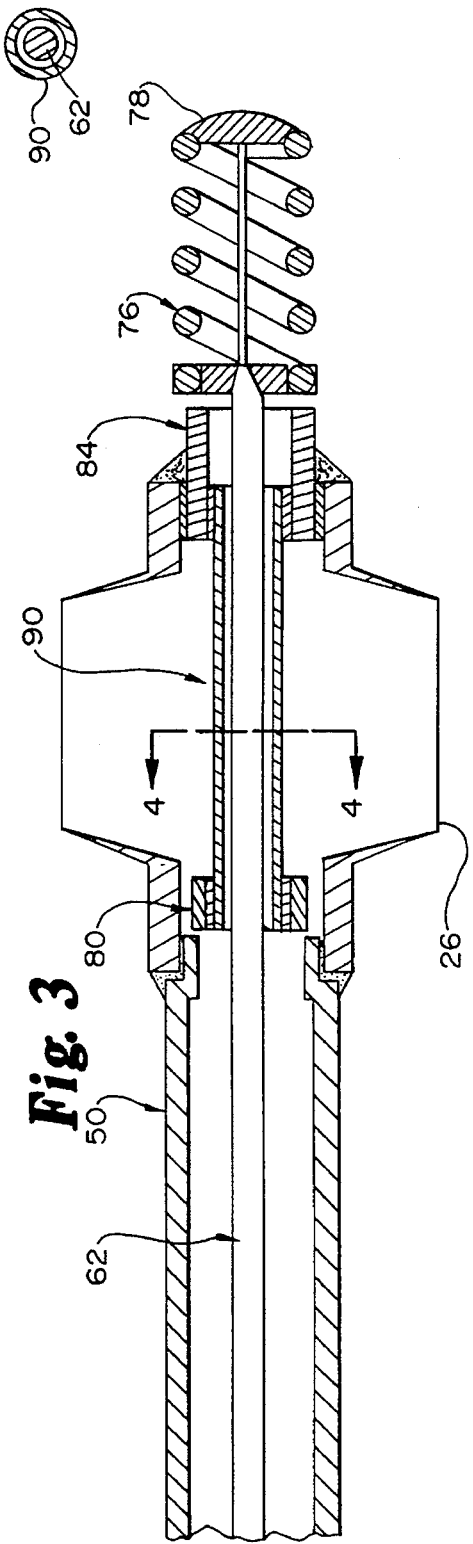

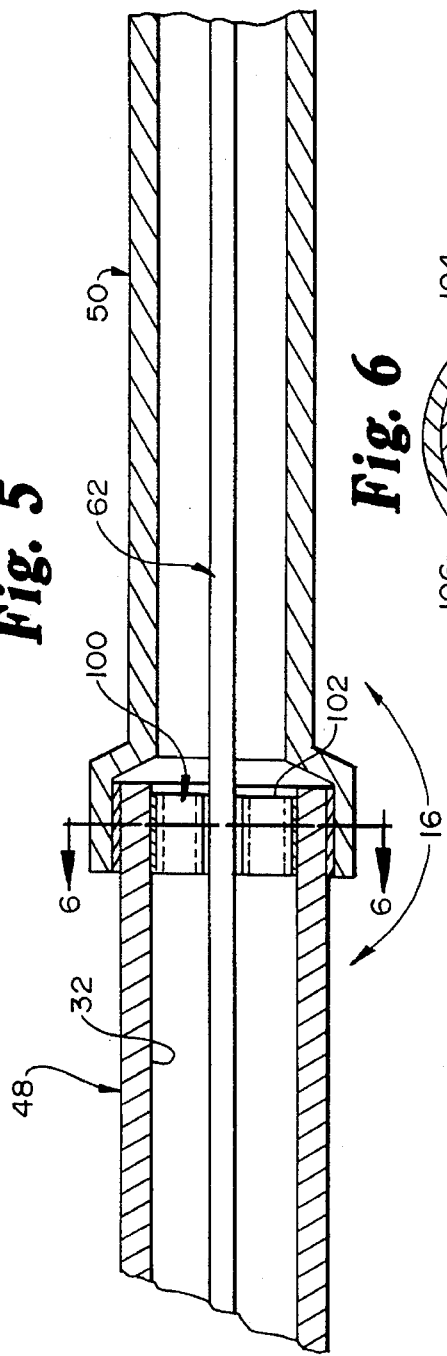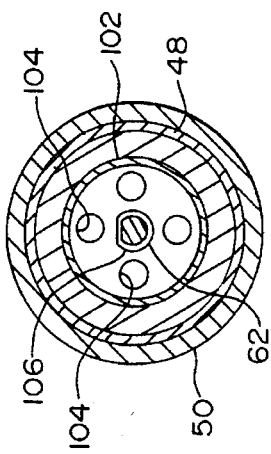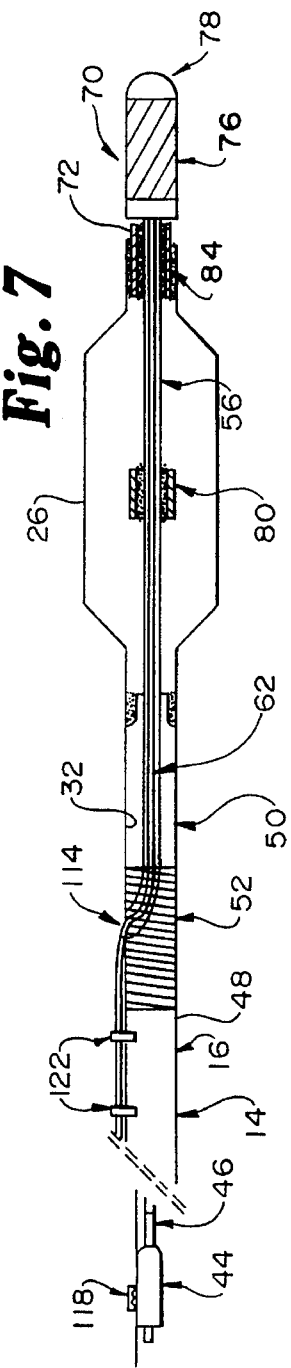

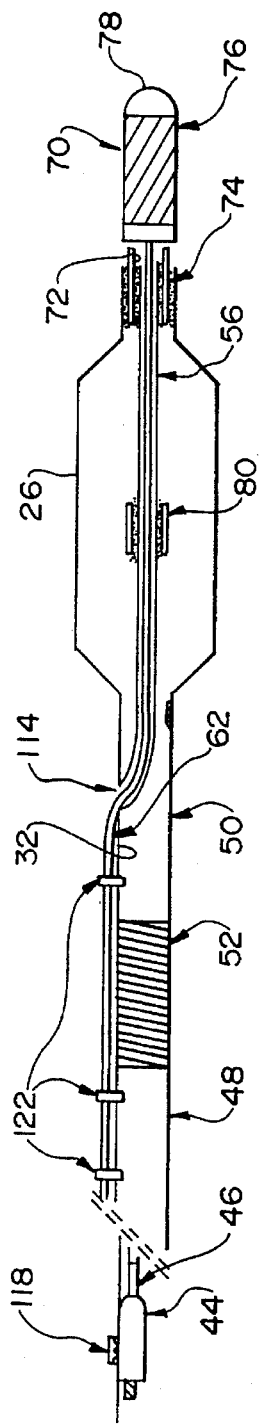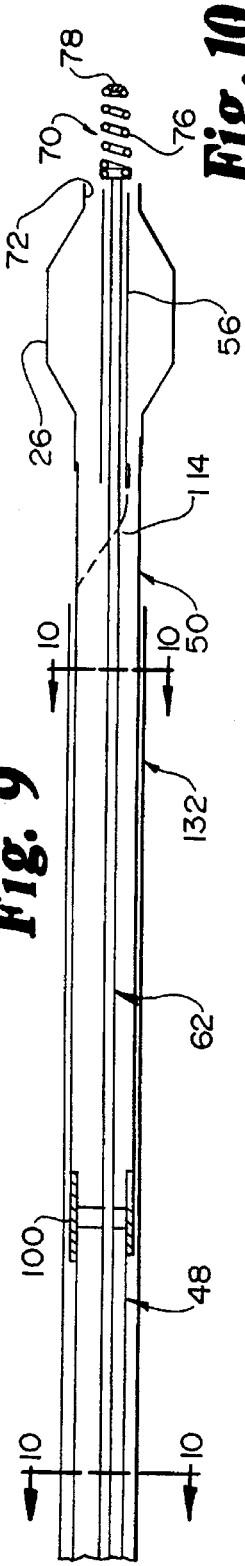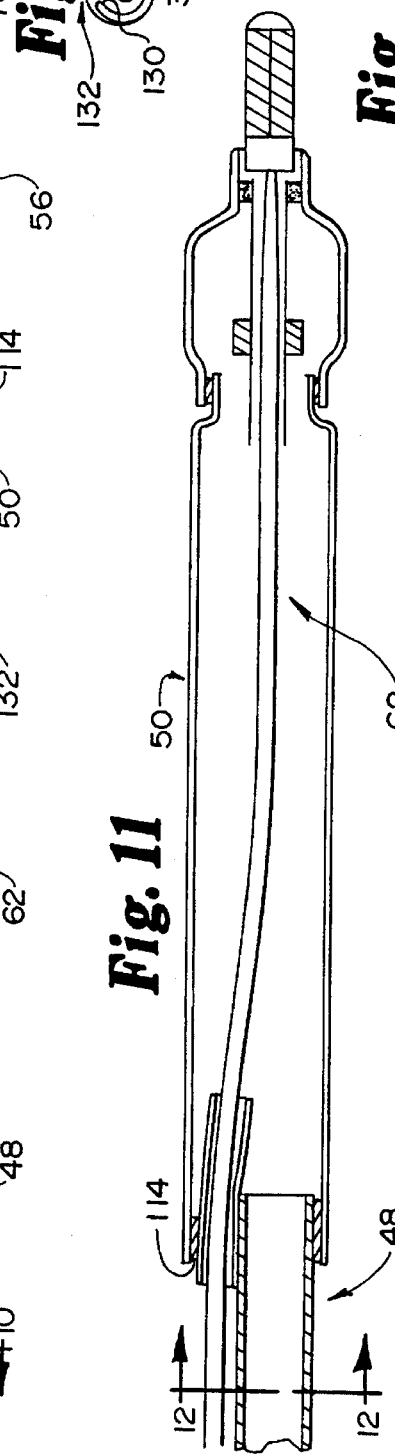

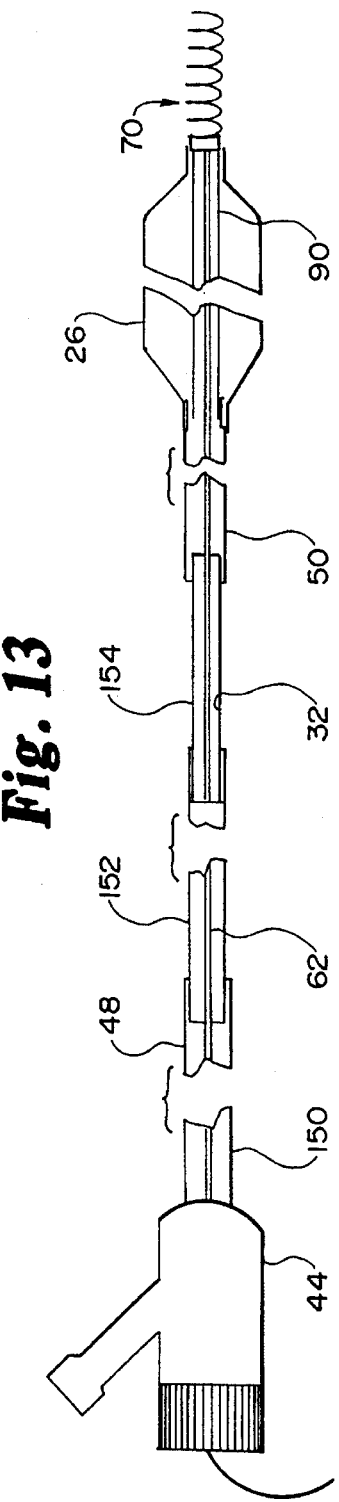
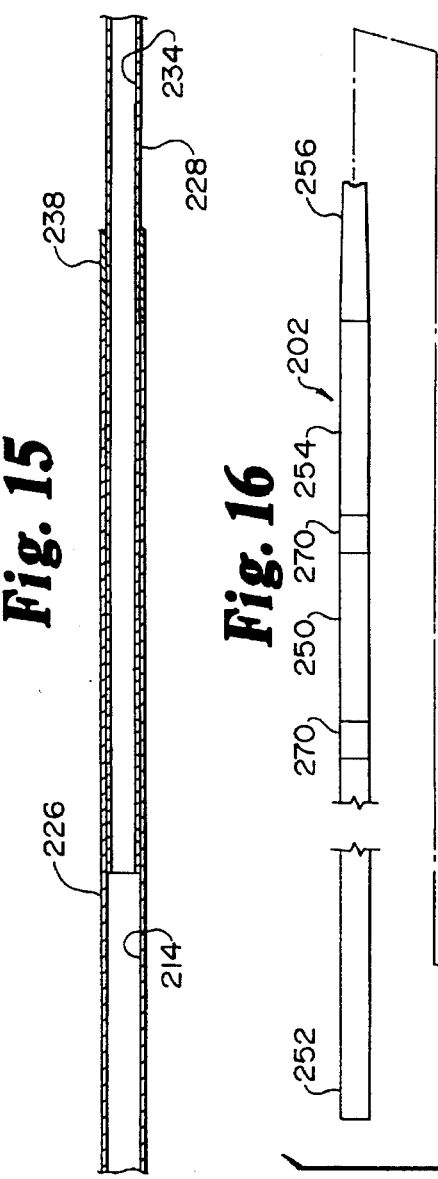
Fig. 13
Fig. 15
Fig. 16

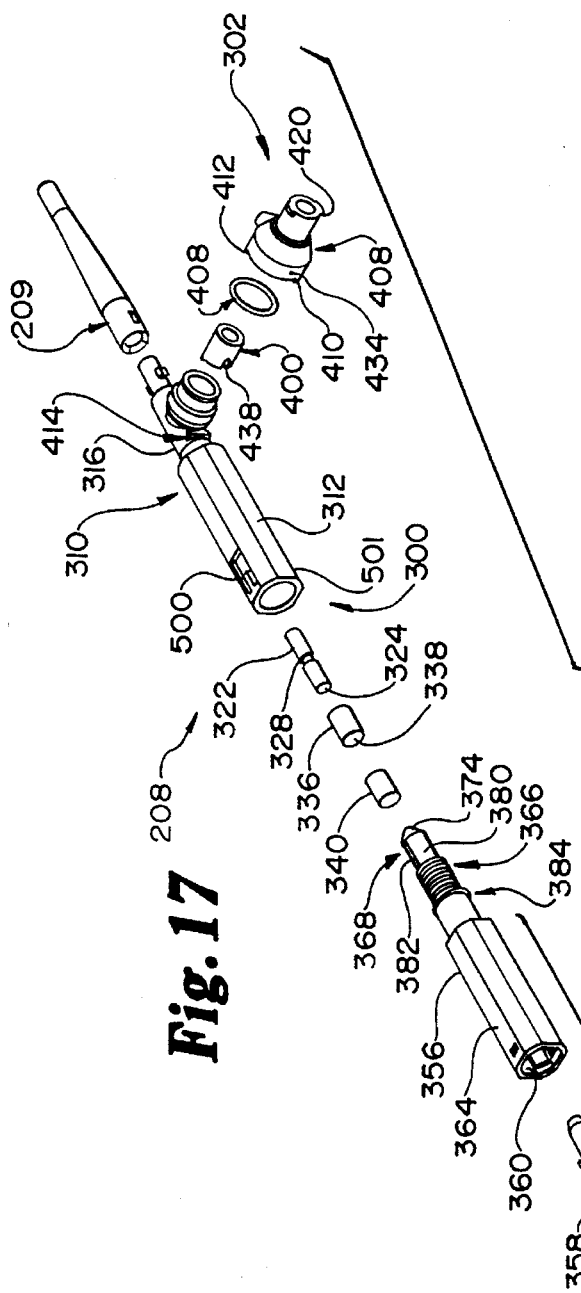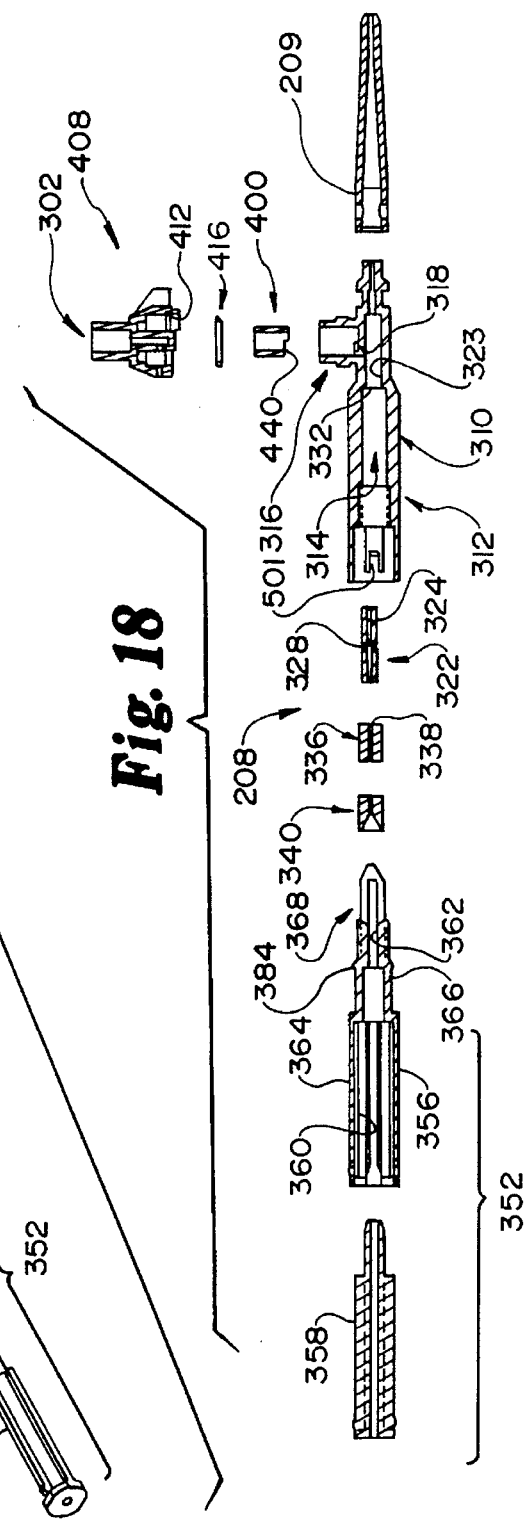

1

INTRAVASCULAR CATHETER AND METHOD FOR USE THEREOF

REFERENCE TO RELATED APPLICATIONS

The present application is a continuation-in-part of Ser. No. 07/843,647, filed Feb. 28, 1992, which is still pending, which was a continuation-in-part of Ser. No. 07/830,479, filed Feb. 4, 1992 which is still which is a continuation of Ser. No. 07/398,756, filed Aug. 25, 1989, now abandoned.

BACKGROUND OF THE INVENTION

This invention relates to an improved intravascular catheter and in particular to an improved intravascular catheter that can have a very low profile and that allows for the exchange of a first catheter for another catheter over a guide wire, and methods for use thereof.

Intravascular catheterization apparatuses have proven to be useful and efficient for both therapeutic and diagnostic purposes. Intravascular catheterization therapies, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic catheter apparatuses, for angiographics, ultrasonic imaging, and Doppler blood flow measurements for example, have been developed to measure or image the extent of an occlusion of a vessel, (e.g., stenosis). These intravascular diagnostic apparatuses may be used in conjunction with the aforementioned therapeutic apparatuses or may be used in conjunction with more invasive techniques such as coronary surgery.

These intravascular therapeutic and diagnostic apparatuses have achieved acceptance because of their effectiveness as well as the fact that they can be used through a minor surgical procedure that is relatively non-disruptive to the patient compared to coronary surgery. These intravascular therapeutic and diagnostic apparatuses rely on the positioning of a catheter device into the vascular system of a patient via an incision at an accessible location which may be remote from the site of the occlusion or stenosis. For example, the accessible location may be the femoral artery at the groin. The intravascular device is then advanced through the incision via the femoral artery to the desired coronary distal site.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is a need for intravascular catheters of very low profile that can be positioned in narrow, tortuous regions of a person's vasculature.

Another important consideration relating to intravascular procedures, such as angioplasty, relates to catheter exchanges. Intravascular therapeutic and diagnostic devices come in various types and sizes suitable for the vessel size and location in which the treatment is to be performed. Sometimes, it becomes necessary to exchange a first therapeutic device for one of a different size after the first device has been positioned or after an unsuccessful attempt to position the first device. This may be necessitated because it becomes apparent that the first device is the wrong size or because it is determined that additional therapeutic or diagnostic procedures with a different size or type of device is required.

Several different types of catheter constructions have been developed for positioning intravascular therapeutic or diagnostic catheters through a patient's vasculature. One type of catheter design, commonly referred to a fixed-wire type catheter, includes a non-removable wire tip attached on a distal end of the intravascular catheter. The wire tip facilitates maneuvering the catheter to the desired vessel site. A disadvantage of the fixed-wire type catheter that is if it becomes necessary to exchange a first catheter for a second catheter, the maneuvering procedure must be repeated for the second catheter. As mentioned above, this can be sometimes a tedious and difficult procedure.

Another type of catheter design, referred to as an over-the-wire type catheter, includes a central lumen through the intravascular device that can accommodate a separate guide wire that is movable, and removable, in relation to the catheter to facilitate positioning the catheter in a remote vessel location over the guide wire. In the over-the-wire construction, the catheter includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel. The guide wire may then be withdrawn proximally through the lumen of the catheter or may be left in place extending from the distal end of the catheter during the procedure.

The over-the-wire type catheter facilitates exchanges. In order to exchange a first over-the-wire intravascular catheter with another, it is preferred not to lose a hold on the proximal end of the guide wire as the catheter is withdrawn over the proximal end of the guide wire. An intravascular catheter with an over-the-wire construction can be exchanged while leaving the distal tip of the guide wire in place by using an exchange wire which is a guide wire having a long length (e.g. 300 cm) so that a sufficiently long proximal portion of the guide wire extends out of the proximal end of the catheter so that the entire catheter can be withdrawn out completely over the wire while maintaining a hold on a proximal portion of the wire. Another way to perform an exchange with an over-the-wire type intravascular catheter is by using a guide wire extension.

A variation of the over-the-wire type catheter that facilitates exchange of a first intravascular catheter with another is the single-operator exchange type design construction. With the single-operator construction, the guide wire occupies a position adjacent to the intravascular catheter along proximal and middle portions of the catheter and enters into a short guide wire lumen of the catheter via an opening in the catheter at a location in a distal portion of the catheter. With this type of design, the catheter can be positioned in the patient's vessel by positioning a guide wire in the desired location and advancing the catheter device over the wire. However, in the event that it becomes necessary to exchange the single-operator catheter, the catheter can be withdrawn proximally while the distal tip of the guide wire is left in position in the vessel site. Because the proximal end of the guide wire and the proximal end of the catheter are adjacent to each other, the proximal end of the guide wire can be held so that the position of the distal end of the guide wire in the patient's vessel can be maintained. With this type of catheter, it is necessary that the distance from the distal end of the catheter to the proximal guide wire lumen entrance is less than the length of the guide wire that extends proximally out of the guiding catheter.

Although intravascular catheters, such as the over-the-wire type and the single-operator type, that employ a separate guide wire provide advantages relating to exchanges, these types of catheters obtain this advantage at the expense of size. In order to accommodate the separate guide wire, a separate guide wire lumen must be provided through at least a portion of the catheter. This element unavoidably increases the overall dimensions of the catheter to at least some degree compared to the fixed-wire type catheter.

Accordingly, there is a need for an improved balloon dilation catheter that facilitates catheter exchange over a guide wire, but that can possess the very small profile of a fixed-wire type catheter.

SUMMARY OF THE INVENTION

The present invention relates to an intravascular catheter and a method for use thereof comprising an elongate shaft having an inflation lumen extending therethrough, a dilation balloon connected to and located at the distal portion of the shaft and communicating with the lumen, a small profile core wire extending through at least the intravascular implement and having a distal portion that extends distally from intravascular implement through a distal core wire opening located distally of the balloon and further in which the core wire is movable relative to the elongate shaft to allow withdrawal of the elongate shaft and the balloon while leaving the core wire positioned intravascularly, and a tip member connected to the core wire in a region thereof distal of the location at which the core wire extends distally of the core wire opening, the tip member having a profile larger than the opening.

BRIEF DESCRIPTION OF THE FIGURES

FIG. 1 is a sectional side elevational view of a first preferred embodiment of a balloon dilation catheter of the present invention.

FIG. 2 is a sectional side elevational view of a second preferred embodiment of a balloon dilation catheter of the present invention.

FIG. 3 shows a longitudinal sectional view of a distal portion of the embodiment of the embodiment depicted in FIG. 2

FIG. 4 shows a sectional view of the along lines A–A' in FIG. 3.

FIG. 5 shows a longitudinal sectional view of an intermediate portion of the embodiment of the embodiment depicted in FIG. 2.

FIG. 6 shows a sectional view of the along lines B–B' in FIG. 5.

FIG. 7 is a sectional side elevational view of a third preferred embodiment of a balloon dilation catheter of the present invention.

FIG. 8 is a sectional side elevational view of a fourth preferred embodiment of a balloon dilation catheter of the present invention.

FIG. 9 is a sectional side elevational view of a fifth preferred embodiment of a balloon dilation catheter of the present invention.

FIG. 10 shows a sectional view of the along lines A–A' in FIG. 9.

FIG. 11 is a sectional side elevational view of a sixth preferred embodiment of a balloon dilation catheter of the present invention.

FIG. 12 shows a sectional view of the along lines A–A' in FIG. 12.

FIG. 13 is a sectional side elevational view of a seventh preferred embodiment of a balloon dilation catheter of the present invention.

FIG. 15 depicts a section of a distal portion of the catheter of FIG. 14 shown in an uninflated condition (shown without the balloon portion for the sake of clarity) such as during positioning of the catheter.

FIG. 16 is a broken side view partially in section of the guide wire of the embodiment of FIG. 14.

FIG. 17 is an exploded perspective view of the manifold assembly in FIG. 14.

FIG. 18 is an exploded side view of the manifold assembly of FIG. 17.

DETAILED DESCRIPTION OF THE PRESENTLY PREFERRED EMBODIMENTS

Figure 14:
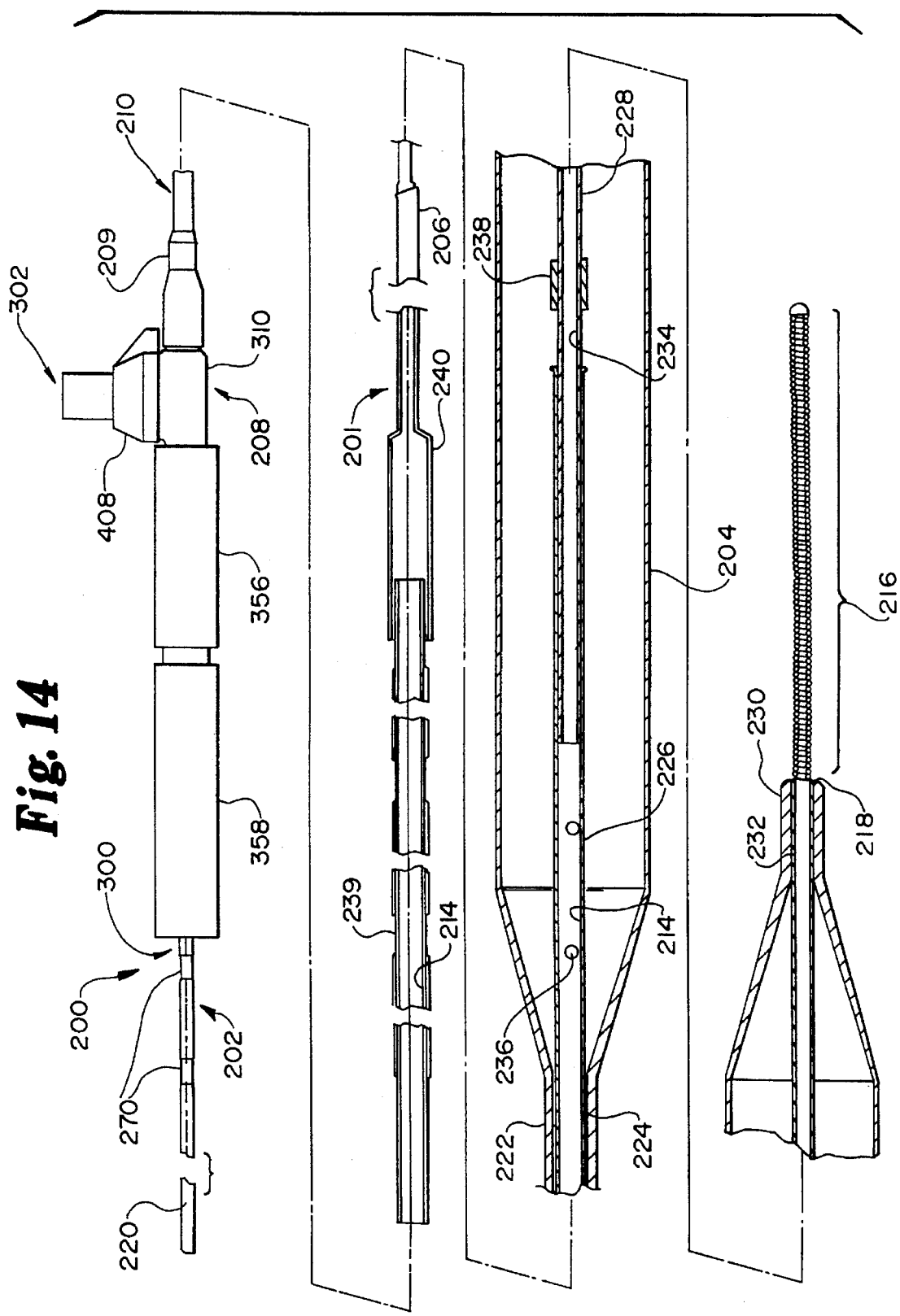
FIG. 14 is a broken longitudinal sectional view depicting another embodiment of the present invention.

Embodiments of the present invention described herein are dilation balloon catheters for use in PTCA procedures. It should be understood that these embodiments may be adapted to other types of intravascular therapeutic devices, such as atherectomy catheters, as well as diagnostic catheters, such as ultrasonic catheters.

I. FIRST PRESENTLY PREFERRED EMBODIMENT

Referring to FIG. 1, there is depicted a PTCA balloon dilation catheter 10 according to a first embodiment of the present invention. The balloon dilation catheter 10 includes an elongate catheter shaft 14 formed of a tubular member 16 having a proximal portion 18 and a distal portion 22. A dilation balloon 26 is located at and connected to the distal portion 22 of the catheter shaft 14. The balloon 26 can be formed from a polyolefin copolymer or other polymer material. For example, in one embodiment, the balloon 26 is formed of a polyolefin copolymer (such as that sold by DuPont under the tradename SURLYN as Resin No. 8527) using secondary treatment with 5 to 50 Mega-rad electron beam irradiation to enhance strength in the region of the balloon 26. The balloon 26 is provided in a variety of conventional sizes suitable for PTCA use.

Extending through the catheter shaft 14 and specifically through the outer tubular member 16 is a first lumen 32. The dilation balloon 26 is in fluid communication with the first lumen 32 of the catheter shaft 14. Inflation fluid is conveyed via the first lumen 32 from an inflation port 40 of a proximally located manifold 44 to inflate the balloon 26 and therefore dilate a vessel in a conventional manner known in the art. Located around the outer tubular member directly distal of the manifold 44 is a strain relief member 46. The strain relief member 46 may be piece of polymeric tubing and have a length of 5 to 10 cm.

In this embodiment, the outer tubular member 16 of the catheter shaft 14 is formed of two portions. A proximal portion 48 of the outer tubular member 16 is formed of a strong, relatively rigid material, such as a stainless steel hypotube formed of type 304 stainless steel. A distal portion 50 of the outer tubular member 16 is formed of a relatively flexible material, such as a polymeric material like a polyolefin copolymer or polyethylene. In a preferred embodiment, the distal portion 50 is formed of polyethylene and in particular a high density polyethylene (HDPE). The proximal portion 48 and the distal portion 50 may be connected together by a bonding means such as an adhesive or a mechanical fit. In a preferred embodiment, the proximal portion 48 of the tubular member 16 has an outer diameter of 0.028 inches, an inner diameter of 0.022 inches, and a length of 105 cm. The distal portion 50 of the tubular member 16 has an outer diameter of 0.025 inches, an inner diameter of 0.019 inches, and a length of 30 cm.

As an alternative construction, the proximal portion 48 of the shaft 14 can be made of a material other than stainless steel. One alternative material that can be used for the shaft is a superelastic alloy. These alloys are also commonly referred to as shape memory alloys. Such an alloy is Tinel® which is available from Raychem, Inc of Menlo Park, Calif. Other materials that offer similar properties include nickel-titanium shape memory alloys available from Shape Memory Applications, Inc. of Sunnyvale, Calif. Nitinol is another such alloy. These materials are available as tubing having high elasticity resulting in a kink-resistant catheter shaft.

Tubing of these superelastic alloys can be used for both the proximal and distal portions of the catheter shaft. If the proximal portion 48 is made of tubing of a superelastic alloy, it preferably has an outer diameter of 0.028 and a wall thickness of 0.002 to 0.003. If the distal portion 50 is made of tubing of a superelastic alloy, it preferably has an outer diameter of 0.020 and a wall thickness of 0.001 to 0.002. Because these materials are difficult to solder or braze, it may be preferred to join them to other substrates with adhesives. Also, in order to provide the tubing in the dimensions necessary for use, the materials may be processed by a centerless grinding operation.

Referring again to FIG. 1, a kink resistant member 52 is preferably located at and distally of the connection between the proximal and distal portions to provide for a transition in stiffness between the relatively rigid proximal portion 48 and the relatively flexible distal portion 50. In one embodiment, the kink resistant member 52 is formed of a spring coil extending across the connection location. In a preferred embodiment, the kink resistant member is formed of a stainless steel coil that extends distally into the distal portion 50 approximately 5 cm. In a preferred embodiment, the spring coil is sized to closely fit in the lumen 32 of the outer tubular member 16. The kink resistant member 52 may be bonded to the outer tubular member 16 or may be positioned by a press or mechanical fit. In alternative embodiments, the kink resistant member 52 may be formed by a wire extending distally of the proximal portion 48, and in particular, a tapered wire.

Located in the first lumen 32 is an inner tubular member 56. The inner tubular member 56 also has a lumen, i.e., second lumen 58, extending therethrough. The tubular member 56 extends through both the distal 50 and proximal 48 portions of the catheter shaft 14 and through the balloon 26. The inner tubular member 56 occupies only a portion of the first lumen 32 thereby providing an annular region between the outer tubular member 16 and the inner tubular member 56 to allow for the conveyance of inflation fluid therein. In a preferred embodiment, the inner tubular member 56 is formed of a relatively flexible material such as a medium density polyethylene. In a preferred embodiment, the inner tubular member 56 has an outer diameter of 0.012 inches and an inner diameter of 0.010 inches and has a length of 140 cm.

Located in the lumen 58 of the inner tubular member 56 is a core wire 62. In this embodiment, the core wire 62 is a very low profile core wire. For example, in a preferred embodiment, the core wire has a diameter less than 0.010 inches, and preferably the core wire has a diameter of 0.006 to 0.008 inches. The core wire 62 extends through the catheter shaft 14 in the inner tubular member lumen 56 and extends proximally of the manifold 44 from a second port 66 thereof. A distal portion 70 of the core wire 62 extends distally from the catheter shaft 14 from a distal opening 72 located distally of the balloon 26. In this embodiment, the distal opening 72 communicates with the lumen 58 of the inner tubular member 56. The core wire 62 preferably has a uniform outer diameter and is tapered distally. In a preferred embodiment the core wire is made of type 304 stainless steel.

Located at and connected to the distal portion 70 of the core wire 62 that extends distally of the balloon 26 is a tip member 76. The tip member 76 is preferably formed of a coil spring joined to the core wire 62. In a conventional manner, the core wire 62 is processed to have a reduced and flattened profile underneath the coil spring to provide additional flexibility. The tip member 76 is preferably formed of a radiopaque material such as platinum, although other materials, such as stainless steel or even non-metallic polymers may be used as well. The tip member 76 may be connected to the core 62 wire by brazing, soldering an adhesive, mechanical fit, or other connecting means. The tip member 76 provides for a flexible, deformable tip for advancing and positioning the catheter 10 intravascularly with minimal trauma to the vessel. Located at the distal end of the tip member 76 is a rounded tip 78 which may be formed of solder or other material in a manner known in the art.

The tip member 70 is sized to conform closely in characteristics to a flexible spring tip incorporated on conventional fixed wire catheters to take advantage of the skills and familiarity already developed by practicing physicians with such conventional fixed wire type catheters. Accordingly, the spring tip is constructed so that it can be bent or otherwise formed, e.g. in a "J" shape, to facilitate positioning into the desired location of the artery.

Located in the region of the balloon 26 is a marker 80. The marker 80 is preferably formed of a small band or coil of radiopaque material such as platinum, gold, etc., that is bonded to the inner tubular member 56 directly underneath the balloon 26. The marker may be bonded by any conventional means, such as a mechanical fit, adhesives, etc. The marker 80 is used in a conventional manner to assist the physician to locate and position the catheter fluoroscopically. Alternatively, the marker may be located at other positions, such as at the distal or proximal balloon waist areas, or multiple markers may be incorporated.

At the location at which the distal portion of the balloon 26 connects to the elongate shaft 14, there is a strain relief member 84. The strain relief member 84 may be a relatively short piece of polymeric tubing connected to the exterior of the inner tubular member 56 directly underneath the distal waist portion of the balloon 26. Thus, the balloon 26 is bonded to the strain relief member 84 which in turn is bonded to the inner tubular member 56. The strain relief member 84 facilitates the connection of the flexible distal waist of the balloon 26 to the flexible inner tubular member 56 by reducing the bond gaps between the distal balloon waist and the shaft. The strain relief member 84 also provides a transition from the relatively flexible spring tip to the relatively stiff balloon bond site. Also, the strain relief member acts like a funnel to facilitate loading of the core wire into the inner tubular member 56 such as during a catheter exchange.

The manifold 44 incorporates a securing means 88 to fix the proximal portion of the small profile core wire 62. When secured, the core wire 62 is fixed relative to the manifold both axially and rotationally. When so fixed, the core wire 62 and the elongate shaft 14 will function similarly to a conventional fixed wire type catheter. The securing means 88 is preferably an easy to manipulate device that the physician can readily operate with one hand. Clamping devices for such a purpose are conventional and known to those of skill in the art. For example, the securing means 88 may include an annular ring having internal threads that engage corresponding external threads on the manifold body. Tightening of the annular member compresses a resilient gasket in an axial direction thereby causing it to clasp the core wire proximal end extending therethrough.

An optional feature of this embodiment is a provision for torque transmission between the shaft 14 and the core wire 62. This feature is particularly advantageous because of the very small diameter of the core wire. This feature may be provided by incorporation of any of the torque transmission embodiments disclosed in copending application Ser. No. 07/583,437 filed Sep. 17, 1990, the entire disclosure of which is specifically incorporated herein by reference. In particular, it is preferred to incorporate a torque transition feature into this embodiment by forming a portion of the core wire 62 with an other-than-round profile in the region corresponding to the kink resistant member 52. Similarly, in the portion of the inner tubular member 56 corresponding to this region, the profile of the second lumen 58 corresponds to the other-than-round shape of the core wire exterior profile so that torque can be transmitted to the distal portion of the core wire by rotation of the proximal end of the outer tubular member 16. It is preferred that the other-than-round external profile of the core wire 62 extend a distance along the core wire to allow advancing the core wire tip distally of the elongate shaft while still providing for torque transmission from the shaft to the core wire for steering purposes.

Operation and handling of the balloon catheter 10 would be similar to that of fixed-wire balloon catheters. Accordingly, the balloon catheter 10 may be packaged with the core wire 62 already positioned in the shaft 14. Before use, the core wire 62 may be fixed proximally by the securing means 88. When the core wire is so fixed, the balloon catheter 10 can be positioned and used in the same or similar manner as fixed wire conventional balloon catheters. Moveover, like conventional fixed wire balloon catheters, the balloon catheter can possess a low profile. Further, when used with the torque transmission feature, as discussed above, the balloon catheter 10 can also possess handling characteristics similar or identical to conventional fixed wire type catheters.

However, the balloon catheter 10 provides a significant advantage not afforded by conventional fixed wire catheters. The balloon catheter 10 allows for the exchange of a first catheter for another while leaving a wire in place in the vascular region thereby facilitating catheter exchanges. Such an exchange may be required for example when it is determined that a balloon of a different size is needed or if a different type of intravascular catheter device is appropriate. This is advantageous for example when the wire is in position past a stenosis that is difficult to cross. Thus, the balloon catheter 10 also provides the advantage of exchangability of over-the-wire type catheters.

With a balloon catheter of the over-the-wire type, there have in the past been two conventional ways to accomplish a catheter exchange while leaving the guide wire in position in the vascular system. One way is to use a separate exchange wire and another way is to use a guide wire extension that fits onto the proximal end of the guide wire to allow the catheter to be withdrawn completely over both the guide wire and the extension wire, However, these procedures can be difficult. For example, use of an exchange wire requires withdrawal of the first wire and substitution of the exchange wire—a procedure that can be time consuming. Connection of a guide wire extension can also be tedious and requires handling of considerable lengths of wire outside of the body of the patient. Moreover, extension wires may be difficult to implement with a very small diameter wire, for example 0.006 to 0.008 inches. Further, with a very small diameter wire, it can be difficult to provide sufficient pushability over the combined length of the guide wire and the extension wire to perform a catheter exchange. Accordingly, with previous guide wire designs, the requirement to provide for connection of an extension wire has to some degree limited the extent to which the guide wire profile could be reduced.

In the present embodiment, the core wire 62 has a profile that is significantly smaller than previous conventional guide wires. With a core wire of the present embodiment, it is preferred not to provide for a proximal guide wire extension for the purpose of effecting catheter exchanges. Instead, a catheter exchange can be accomplished by means of a guide wire captivation apparatus and method as described in application Ser. No. 07/398,765 filed Aug. 25, 1989. For example, it is preferred to use a Trapper catheter exchange device, manufactured by SciMed Life Systems of Maple Grove, Minn. With the use of a guide wire captivation device, even a core wire having a very small profile can be readily fixed in a vessel location. Accordingly, the wire size need not be constrained for purposes of providing for an extension wire.

Referring again to FIG. 1, in the present embodiment, using a guide wire captivation apparatus, the catheter shaft 16 can be withdrawn entirely from the artery while leaving the core wire 62 in place in the arterial site. A second intravascular catheter, of a different size for example, can then be installed over the core wire 62. This provides the advantage of over-the-wire type catheters. Withdrawal of the core wire 62 through the catheter shaft 14 is of course not provided because the profile of the tip member 70 is larger than that of the distal opening 72 and second lumen 58. The second intravascular catheter would preferably be of a type adapted for use with a small profile core wire.

II. SECOND PRESENTLY PREFERRED EMBODIMENT

Referring to FIGS. 2 to 6, there is depicted a second preferred embodiment of the present invention. This embodiment is also a balloon catheter for performing angioplasty and includes components similar or identical to those described with respect the above embodiment, except as noted below. Similar components in this embodiment are indicated with the same numerals as above.

The embodiment shown in FIGS. 2 through 6 incorporate an innerless construction, i.e. the inner tubular member 56 is omitted in at least a portion of the catheter shaft 14 and a single tubular member provides the functions of both the outer tubular member and the inner tubular member of a conventional coaxial over-the-wire type catheter. This embodiment may be constructed in the manner described in U.S. Pat. Nos. 5,032,113, 5,085,636, or in copending application Ser. No. 07/776,559 filed Oct. 15, 1991, the entire disclosures of which are incorporated herein by reference.

In this embodiment, the proximal portion 48 of the tubular member 16 is preferably made of type 304 stainless steel and has an outer diameter of 0.024 inches and a wall thickness of 0.003. The distal portion 50 of the tubular member 16 is preferably made of high density polyethylene and has an outer diameter of 0.024 inches and a wall thickness of 0.025 inches. If the proximal portion 48 is made of tubing of a superelastic alloy, it preferably has an outer diameter of 0.023 and a wall thickness of 0.002 to 0.003. If the distal portion 50 is made of tubing of a superelastic alloy, it preferably has an outer diameter of 0.018 and a wall thickness of 0.001 to 0.002.

Referring to FIG. 2, the outer tubular member 16 extends from the manifold 44 to attach to the balloon 26. In this embodiment, a sleeve member 90 is located around the core member 62 in the portion of the catheter corresponding to the location of the balloon 26. The sleeve member 90 may be joined to the distal waist of the balloon 26. The sleeve member 90 terminates proximally at a location distal of the manifold 44. Preferably, the sleeve member 90 terminates proximally at a location 92 corresponding to the proximal balloon waist 94. The proximal end of the sleeve member 90 preferably is connected (e.g. by an adhesive) on one edge to a portion of the proximal balloon waist. Proximally of the location 92, the core wire 62 occupies the same lumen 32 that is used for conveyance of inflation fluid. The sleeve member 90 defines a lumen 96 that communicates with the distal opening 72 and which is occupied by a portion of the core wire 62. The sleeve member lumen 96 has a sufficiently low clearance around the core wire 62 such that the balloon 26 can be inflated to dilation pressures with little or no loss of inflation fluid through the lumen 96 with the core wire in place. Further, the sleeve member 90 provides for free core wire movement—both axially and rotationally—including when the catheter is positioned in tortuous arterial anatomy. In a preferred embodiment, the gap between the core wire 62 and the sleeve member is approximately 0.0001 to 0.0002 inches. (Alternatively, a valving device can be incorporated into the sleeve member 90, as disclosed in copending application Ser. No. 07/776,559). In this embodiment, it is required that the proximal portion of the core wire 62 have a profile that is less than or equal to the sleeve lumen 96 to allow withdrawal of the catheter shaft 14 over the core wire 62.

In this embodiment, the marker member 80 is bonded to the sleeve 90 at a proximal location thereof in the region corresponding to the proximal balloon waist.

Referring specifically to FIGS. 5 and 6, there is illustrated a torque transition member 100 that can be used with this embodiment with an innerless construction. The torque transition member 100 may be formed in a manner similar to that described above with respect to the first embodiment. In the present embodiment with an innerless construction, the torque transmission member comprises a circular insert 102 located in the lumen 32 at the distal end of the proximal portion 48 of the tubular member 16. The insert 102 is fixed to the proximal portion 48 so as to move rotationally therewith. Extending through the insert 102 are one or more apertures 104 to allow conveyance of inflation fluid therethrough. In addition, the insert 102 also includes a keyed aperture 106. The keyed aperture 106 has a flat side, for example, or any shape other than round. The core wire 62 has an outer profile along a portion thereof corresponding to the position of the insert 102 so as to restrict relative rotation between the core wire 62 and the insert 102 (and thereby the shaft 16) when the keyed region of the core wire engages the keyed aperture of the insert 102. Axial movement however is not impeded. Moreover, in a preferred embodiment, the keyed portion of the core wire 62 preferably extends for only a relatively short distance, e.g. 2 cm, so that beyond the keyed region, the core wire 62 has a profile that allows relative rotation with respect to the insert 102 and shaft 16. Therefore, when the physician requires the torque transmission feature, the core wire keyed region is axially aligned with the insert 102 so that torque can be transmitted from the relatively stiff proximal outer tube 48 to the core wire 62.

III. THIRD PRESENTLY PREFERRED EMBODIMENT

Referring to FIG. 7, there is depicted a third preferred embodiment of the present invention. Like the above embodiments, this embodiment is also a balloon catheter for performing angioplasty and includes components similar or identical to those described with respect the above embodiments, except as noted below. Similar components in this embodiment are indicated with the same numerals as above.

This embodiment incorporates a single-operator exchange construction. In this type of construction, the inner tubular member 56 extends proximally from the distal opening 72 to a proximal opening 114 located in a portion of the elongate shaft 14 that is normally within the body of the body during intravascular use. In this embodiment, the proximal opening 114 is located at or close to the connection between the distal portion 50 and the proximal portion 48 of the outer tubular member 16 and in particular, the proximal opening 114 is located through the kink resistant member 52 to enhance the stability of the catheter. In this embodiment the proximal opening 114 is located approximately 12 cm proximally of the proximal end of the balloon 26.

With the single-operator construction, the wire is located adjacent to the catheter shaft 16 proximal of the proximal opening 16. In this embodiment, this portion of the catheter shaft is normally within the guide catheter conventionally used in coronary procedures. Accordingly, the manifold 44 will not include a port through which the wire extends. However, instead there may preferably be a wire lock and release device 118 associated with the manifold 44 to secure and fix the portion of the wire relative to the catheter shaft 16.

With a core wire of very small profile, it may be advantageous to secure the core wire 62 to the catheter shaft 16 proximally of the proximal opening 114. For this purpose a wire containment mechanism 122 may be provided along the catheter shaft 16 proximal of the proximal opening 114. The wire containment mechanism 122 also prevents twisting of the core wire 62 around the catheter shaft 16. In a preferred embodiment, the wire containment mechanism 122 retains the core wire 62 close along the catheter shaft 16 and prevents twisting of the small profile wire around the shaft 16. It is also preferred that the wire containment mechanism 122 allow for at least limited axial movement of the core wire 62 relative to the catheter shaft 16 so that the shaft 16 can be withdrawn while leaving the core wire 62 in place in the arterial site. The wire containment mechanism 122 may be in the form of one or more small wire or plastic clips 124 that extend laterally from the outside wall of the catheter shaft 16 and which maintain the core wire 62 close thereto. Alternatively, the wire containment mechanism 122 may be formed by a series of small magnets located along the catheter shaft 16 that attract the core wire 62 and hold the core wire 62 close thereto. Still a further alternative is to provide a longitudinally extending slit along the exterior surface of the catheter shaft 16. The slit is sized and adapted to allow retaining the core wire 62 within it during intravascular use but to allow easy removal when the catheter shaft it withdrawn proximally.

An advantage of the single-operator construction is that it facilitates catheter exchange. The catheter shaft 14 can be withdrawn while the distal end of the wire 62 is left in place in the arterial site. A catheter exchange may be performed with the single-operator embodiment without the use of a captivation catheter. However, a captivation catheter may be preferred because of the advantages associated with the use of the captivation catheter such as wire tip stability and reduced bleeding back through the guide catheter.

IV. FOURTH PRESENTLY PREFERRED EMBODIMENT

Referring to FIG. 8, there is depicted a fourth preferred embodiment of the present invention. Like the above embodiments, this embodiment is also a balloon catheter for performing angioplasty and includes components similar or identical to those described with respect the above embodiments, except as noted below. Similar components in this embodiment are indicated with the same numerals as above.

Like the previous embodiment, this embodiment incorporates a single-operator exchange construction. In this embodiment, the inner tubular member 56 extends proximally from the distal opening 72 to the proximal opening 114 located in a portion of the elongate shaft 14 that is normally within the body of the body during intravascular use. In this embodiment, the proximal opening 114 is located at or close to the connection between the distal portion 50 of the outer tubular member 16 and the proximal waist portion of the balloon 26. In this embodiment the proximal opening 114 is located approximately 1 cm proximally of the proximal end of the balloon 26 directly in the distal portion. With this construction, the proximal opening 114 may be located distal of the distal end of the guide catheter during intravascular use.

In this embodiment, it may be advantageous to strengthen the distal portion 50 of the outer tubular member 16 to provide for appropriate pushability and tracking of the catheter. This may be provided by incorporation of a transition member as described in the copending application, entitled "Intravascular Catheter With Distal Guide Wire Lumen and Transition Member" filed on Feb. 10, 1992 (Attorney Docket No. 3570/92), the entire disclosure of which is incorporated herein by reference. Such a transition member may not be required with a catheter of such small profile however or may alternatively be provided by processing the distal portion 50 of the outer tubular member to enhance its stiffness distally.

V. FIFTH PRESENTLY PREFERRED EMBODIMENT

Referring to FIGS. 9 and 10, there is depicted a fifth preferred embodiment of the present invention. Like the above embodiments, this embodiment is also a balloon catheter for performing angioplasty and includes components similar or identical to those described with respect the above embodiments, except as noted below. Similar components in this embodiment are indicated with the same numerals as above.

FIGS. 9 and 10 depict a dilation catheter having a single-operator construction like that of the embodiment shown in FIG. 8. In the embodiment of FIGS. 9 and 10, the core wire 62 is located in a longitudinally extending slot 130 that is formed in and by the exterior surface of both the proximal portion 48 and the distal portion 50 of the outer tubular member 16. In particular, the slot 130 is formed by bending the proximal and distal tubular members 48 and 50 that make up the outer tubular member 16 to define a groove. Located around the shaft 14 from the manifold 44 almost to the proximal wire opening 114 is a sleeve 132. The sleeve 132 may be formed of a polymeric sheath that can be readily slid over the shaft 14. The sleeve 132 also has a slit 134 extending therealong corresponding to the slot 130. The slit 134 in the sleeve 132 can be formed to be wavy or oscillating to facilitate retaining the core wire 62 within the slot 130. The sleeve 132, slit 134 and slot 130 are sized so that the core wire fits snugly within, but can be removed easily.

VI. SIXTH PRESENTLY PREFERRED EMBODIMENT

Referring to FIGS. 11 and 12, there is depicted a sixth preferred embodiment of the present invention. Like the above embodiments, this embodiment is also a balloon catheter for performing angioplasty and includes components similar or identical to those described with respect the above embodiments, except as noted below. Similar components in this embodiment are indicated with the same numerals as above.

FIGS. 11 and 12 depict a dilation catheter having a single-operator construction with a longitudinally extending slot 130 along the catheter shaft 16 like that of the embodiment shown in FIGS. 9 and 10. In the embodiment of FIGS. 11 and 12, the proximal wire opening 114 is located at the proximal end of the distal tubular portion 50 at the connection between the distal tubular portion 50 and the proximal tubular portion 48. The location of the proximal wire opening 114 is similar to that of the embodiment shown in FIG. 7. In the embodiment shown in FIG. 11, the core wire 62 occupies the same lumen 32 used for conveyance of inflation fluid through the distal tubular portion 50. This allows for a further reduction in overall profile of the catheter by elimination of the inner tubular member 52 through the distal tubular portion 50. This embodiment may incorporate a sleeve 140 through the balloon portion 26 of the catheter. The sleeve 140 may be similar to the sleeve 90 described with respect to the embodiment shown in FIGS. 2 through 4.

In this embodiment, a proximal guide wire sleeve 142 is located at the proximal wire opening 114 and extends a short distal distally into the distal tubular member. The proximal wire sleeve 142 has dimensions such that little or no inflation fluid will escape through the sleeve 142 between the wire 62 and the sleeve 142 during inflation of the balloon 26. The sleeve 142 may be constructed to provide a clearance on the order of approximately 0.0001 to 0.0002 inches for this purpose.

In order to ensure that the core wire is guided into the core wire 62 during a catheter exchange, the distal portion of the sleeve 142 may be provided with a funnel-like shape to guide the core wire through the sleeve 142.

The embodiment shown in FIGS. 11 and 12 also includes a longitudinally extending slot 130. Because the core wire 62 is located in the lumen 32 through the distal portion 50 of the tubular member 16, the slot 130 is formed in the exterior surface of only the proximal portion 48 of the outer tubular member 16. This embodiment may also include a sleeve around the shaft 14 from the manifold 44 to almost the proximal wire opening 114 similar to the sleeve 132 as in the embodiment shown in FIGS. 9 and 10.

VII. SEVENTH PRESENTLY PREFERRED EMBODIMENT

Referring to FIG. 13, there is depicted a seventh embodiment of the present invention. This embodiment of the present invention includes an innerless construction like that of the embodiment shown in FIGS. 2 through 6. The embodiment of FIG. 13 provides an alternative means for catheter exchange. In the embodiment of FIG. 13, the proximal tubular portion 48 is formed of two or more sections 150, 152, and 154, that telescope together so that the overall length of the proximal portion 48 can be changed from an extended length for use during dilation and a reduced length for use during exchanges. For this purpose, the proximal portion 48 may preferably be formed of three or more sections each having a length of approximately 30 cm. The sections 150, 152, and 154 are preferably made from stainless steel. Where the sections fit together, an annular rim is formed on the inside surface of the outer and the outside surface of the inner of the telescoping pieces to provide for a fluid tight seal and to prevent the sections from becoming disengaged.

The embodiment of FIG. 13 may be used in the same manner as a conventional dilation catheter. When a need to exchange a first catheter for another arises, the first catheter can be withdrawn by telescoping together the sections 150, 152, and 154 of the proximal portion 48 as the catheter shaft 14 is withdrawn so that the proximal end of the core wire 62 can be securely grasped while the distal end of the core wire is left in position in the arterial site.

VIII. EIGHTH PRESENTLY PREFERRED EMBODIMENT

Referring to FIGS. 14–16, there is depicted a still another embodiment of the present invention. This embodiment is similar in some respects to the embodiment shown in FIGS. 2–4. Referring to FIG. 14, there is a balloon catheter system 200 having a catheter portion 201 and a guide wire 202. The catheter portion 201 includes a dilation balloon 204 located at a distal portion 206 of an elongate shaft 206. A manifold 208 is located at a proximal end 210 of the shaft 206. A strain relief 209 connects over the shaft 206 immediately distal of the manifold 208. The guide wire 202 extends through the elongate shaft 206 of the catheter portion 201 and in particular the guide wire 202 occupies a position in a lumen 214 of the shaft 206. As in the previous embodiments, the guide wire 202 is removable with respect to the shaft 206 of the catheter portion 201 so that the guide wire 202 can be maintained in position in a distal vessel location while the catheter portion 201 is removed and exchanged for another catheter. Also, like the previous embodiments, the guide wire 202 has a distal portion 216 that has a larger profile than a distal guide wire opening 218 of the catheter portion 201 so that removal of the catheter portion 201 from the guide wire 202 for catheter exchange may be effected by withdrawal of the catheter portion 201 from the guide wire 202. Also, as in the previous embodiments, the guide wire 202 is provided with a proximal end 220 that is without a connection for coupling with a guide wire extension.

As in the embodiment depicted in FIGS. 2–4, the embodiment 200 has an innerless construction, i.e., the lumen 214 occupied by the guide wire 202 is also used, at least in part, for conveyance of fluid for inflation of the balloon 204. Because the guide wire 202 and the inflation fluid share a common lumen, at least in part, a seal should be provided to prevent or limit leakage of inflation fluid out the distal opening 218 during inflation of the balloon 204.

Referring to FIG. 14, a proximal waist 222 of the balloon 204 is bonded to a distal portion of the shaft 206 at a location 224. A distal extension or end 226 of the shaft 206 is located inside the balloon 204. A sealing sleeve 228 is received in the distal extension 226 of the shaft and extends distally. The sealing sleeve 228 and the distal extension 226 of the shaft are not bonded together so that the sealing sleeve 228 can slide relative to the shaft distal extension 226. A distal waist 230 of the balloon 204 is bonded to a distal portion of the sealing sleeve 228 at a location 232. The guide wire 202 extends from the distal end of the shaft and through a lumen 234 of the sealing sleeve 228 and out the distal opening 218 formed by a distal end of the sealing sleeve 228. A close tolerance fit between the guide wire 202 and the sealing sleeve 228 as well as between the sealing sleeve 228 and the shaft extension 226 prevent or limit any significant leakage of inflation fluid out through the distal opening 218 during pressurization of the fluid for inflation of the balloon 204.

It is an advantage associated with this embodiment that the distal extension 226 of the shaft is slidable with respect to the sealing sleeve 228. When the balloon is inflated, the balloon expands radially and tends to expand longitudinally as well. This longitudinal expansion upon inflation tends to cause the proximal and distal ends, or waists, of the balloon to move apart. Unless the portion of the catheter underneath the balloon can accommodate this expansion, such expansion can cause stresses on the proximal and distal connections or bonds at the balloon proximal and distal waists. With the embodiment described above, because the shaft 206 and sealing sleeve 228 can move apart when the balloon is inflated, stresses at the connections between the balloon and the shaft or between the balloon and sealing sleeve can be reduced.

One or more openings 236 are located through the shaft extension 226 inside the balloon 204 in order to provide for fluid communication between the lumen 214 and the interior of the balloon 204. These openings 236 allow fluid to pass from the lumen 214 to the interior of the balloon 204 for inflation thereof. These openings 236 are located in a portion of the shaft extension 226 proximal of the location of the proximal end of the sealing sleeve 228 inside the extension 206. In a preferred embodiment, 4 openings are provided each having a diameter of approximately 0.008 inches. These openings 236 are spaced 1 mm apart axially from each other along the shaft extension 226 and each opening is staggered 90° apart circumferentially from an adjacent opening.

A marker 238 is located underneath the balloon 204. The marker 238 is composed of a ring of a radiopaque material such as 90% platinum and 10% iridium. The marker 238 is approximately 0.051 inches in length and 0.0015 inches in thickness. The marker 238 is used in a conventional manner for fluoroscopic observation of the position of the balloon 204. In a preferred embodiment, the marker 238 is also used to transmit an axially applied force from the shaft 206 and shaft extension 226 to the sealing sleeve 228. In a preferred embodiment, the marker 238 is bonded to the sealing sleeve 228 at location so that it forms a shoulder against which a distal end of the shaft 206 can abut, as shown in FIG. 15. Thus, when a pushing force is applied to the elongate shaft 206 at the proximal end by the physician for example during positioning of the catheter system 200, the force will be transmitted across the slidable-fitting shaft extension 226 and sealing sleeve 228 to the distal portion of the catheter.

This feature enhances the maneuverability of the catheter. Because maneuverability is required when the balloon catheter 200 is being positioned, the location of marker 238 abutting the distal end of the shaft extension 226 is associated with the balloon 204 in its uninflated condition, as shown in FIG. 15. Inflation of the balloon 204 will tend to cause the proximal and distal ends of the balloon to move apart. Because the sleeve 228 and the shaft extension 226 can slide relative to each other, they will also tend to move apart such that when inflated, the marker 238 will not be immediately adjacent the distal end of the shaft extension 226, as shown in FIG. 14. Upon deflation of the balloon 204, the proximal and distal ends of the balloon 204 will tend to come together again and the marker 238 will also return to an abutting position against the distal end of the shaft extension 226.

In a preferred embodiment, the sealing sleeve 228 may be provided in a length so that approximately 0.023 to 0.062 inches of the sealing sleeve 228 extends into the distal extension 226 of the shaft. The sealing sleeve 228 possesses an outer diameter of approximately 0.013 inches and an inner diameter of approximately 0.011 inches. In a present embodiment, the sealing sleeve is composed of polyimide with a coating of PTFE (e.g. Teflon) on an inner surface thereof. The balloon 204 is made of an irradiated polyolefin copolymer such as Surlyn available from DuPont or a low or medium compliance material such as a PET. The balloon may be provided in various diameters and lengths. The shaft 206 is composed of a two-piece construction with a proximal portion 239 composed of 304 stainless steel and a distal portion 240 composed of high density polyethylene. The shaft 206 has a length of approximately 66.5 inches from the manifold 208 to the proximal end of the balloon 204. The shaft 206 has a proximal outer diameter of approximately 0.023 inches and a distal outer diameter of 0.026 inches with a portion in an intermediate section where the proximal and distal pieces overlap having an outer diameter of approximately 0.033 inches. The wall thickness of the shaft 206 is approximately 0.0025 proximally and 0.003 inches distally. The distal extension 226 of the shaft that extends into the balloon is preferably formed of the same piece of material as the portion of the shaft 206 immediately proximal therefrom. Alternatively, the shaft extension 226 may be made of a separate piece of tubing that is connected to the shaft 206 at or on either side of the proximal balloon waist. The length of the distal extension 226 of the shaft that extends into the balloon is sufficient to allow for a length for the inflation openings 236 as well as another length for an overlapping region where the proximal portion of the sealing sleeve 228 is received in the distal end of the shaft extension 226. The length of the distal shaft extension 226 is thus dependent on the size of the balloon and accordingly will vary with different balloon sizes. With a typical range of balloon sizes, the length of the shaft distal extension 226 distal of the proximal balloon waist is approximately 0.47 to 1.14 inches. The inner diameter of the shaft distal extension 226 in the portion that receives the sealing sleeve is approximately 0.014 inches.

As mentioned above, the guide wire 202 is removable with respect to the shaft 206 by withdrawal of the shaft 206 from the guide wire 202. Referring to FIG. 16, there is depicted a preferred embodiment of the guide wire 202 especially for use with the embodiment shown in FIG. 14 and 15. The guide wire 202 includes the distal portion 216 and a proximal portion 244. In a preferred embodiment, the proximal portion 244 of the guide wire 202 includes a core portion 246 and a wire sleeve portion 248 that is located around at least a part of the core portion 246. The core portion 246 is made of a high tensile stainless steel such as 304 stainless steel and the wire sleeve portion 248 is made of a polymer, such as PTFE (e.g. Teflon). The polymer may be heat shrunk onto the core wire 246. At least a portion of the guide wire 202 is coated with a low friction coating such as silicone. In a present embodiment, a silicone coating is applied to the distal portion 216 and a distal region of the proximal portion 244. A proximal region of the proximal portion 244 of the guide wire is left uncoated with the silicone. The uncoated proximal region of the guide wire 202 is approximately 18 inches in length. The guide wire sleeve portion 248 is located immediately proximal of the distal portion 216 of the guide wire 202. The guide wire sleeve portion 248 extends along a section of the proximal portion 244 of the guide wire 202 that corresponds approximately to the section of the guide wire 202 that is located in the sealing sleeve 228 of the catheter portion 201 during use. In a present embodiment, the guide wire sleeve portion 248 extends for approximately 6.50 inches proximally from the distal portion 216 of the guide wire 202. The guide wire sleeve portion 248 helps improve the fluid seal between the sealing sleeve 228 of the catheter portion 201 and the guide wire 202. For this purpose, the guide wire sleeve portion 248 is preferably made of a material that forms a close and fluid sealing fit with the sealing sleeve 228.

The guide wire 202 has an overall length greater than that Of the catheter portion 201. Specifically, the guide wire 202 has a length such that the distal portion 216 extends distally from the distal end of the catheter portion and at least a portion of the proximal portion 244 extends proximally from the proximal end of the catheter portion 201. In a present embodiment, the guide wire 202 has a length of approximately 75 inches. As mentioned above, the distal portion 216 has a larger profile than the proximal portion 244 including the wire sleeve 248. The proximal portion 244 should have a profile that is not larger than the distal opening 218 of the catheter 201 so that the shaft 206 can be withdrawn proximally over the guide wire 202. In a preferred embodiment, the proximal portion 244 of the guide wire is not larger than approximately 0.011 inches. In a preferred embodiment, the proximal portion 244 does not have a uniform profile but instead includes a first section 250 extending from the proximal end 252 for length of approximately 62 inches and having a diameter of approximately 0.010 inches, a second section 254 immediately distal of the first section and having a length of approximately 2.00 inches that tapers down to approximately 0.0067 inches, a third section 256 located immediately distal of the second section and having a uniform diameter of approximately 0.0067 inches and a length of approximately 5 inches, a fourth section 258 immediately distal of the third section and having a length of approximately 5 inches that tapers down to approximately 0.0055 inches, and a fifth section 260 immediately distal of the fourth section and having a length of approximately 2.156 inches. A radiopaque coil spring 262 is affixed to the distal end of the core wire. The coil 262 is approximately 1–2 cm in length and surrounds a distal portion 264 of the fifth section 260 of the core wire. The core wire is preferably flattened in the most distal section along the portion that is located within the coil. The coil spring 262 and core wire 246 form the distal section 216 of the guide wire 202. The coil spring 262 has an outer diameter of approximately 0.015 inches. The core wire 246 and/or the sleeve portion 248 may be centerless ground to provide the appropriate tolerances.

In a preferred embodiment, one or more markers 270 may be located along a proximal portion of the guide wire 202.

These markers are located along a section of the proximal portion 250 of the guide wire that would extend proximally from the manifold 208. By observation of the positions of these markers 270 relative to the manifold 208, the physician can determine the extent that the distal portion 216 of the guide wire 202 is extended past the distal end of the catheter portion 201. Also, the physician can determine when the guide wire sleeve 248 is in alignment with the sealing sleeve 228 so that the balloon can be inflated. In a preferred embodiment, there are two markers. One of the markers is located approximately 60 inches proximal of the distal portion 216 of the guide wire and another of the markers is located approximately 65.5 inches proximal of the distal portion 216 of the guide wire 202. In a preferred embodiment, each marker is approximately 0.5 inches in length and is applied by means of a biocompatible ink.

In a preferred embodiment, the catheter system 200 can be used in the manner described above in connection with the embodiment of FIGS. 2–4. Prepping the catheter 200 is performed with the guide wire 202 in place in the lumen 214. When prepping the catheter system 200, it is preferable to immerse the balloon 204 in a 50–50 mixture of Renografin and saline when drawing a negative pressure to prevent pulling any air into the distal end of the catheter 201 due to any slight leakage. The guide wire 202 is releasably fixed against relative movement with respect to the catheter portion 201 so that the catheter system 200 can be handled and positioned like a conventional fixed wire balloon catheter. In the event that a catheter exchange is desired, the embodiment provides the advantage unavailable in fixed wire catheters that the guide wire can be Left in position intravascularly while the catheter portion 201 is withdrawn and replaced with another catheter over the same guide wire 202. The second catheter may be any type of catheter compatible with the guide wire 202. The second catheter should be of the type that receives a conventional guide wire in a guide wire lumen. In a preferred embodiment, the second catheter is not necessarily a catheter similar to the catheter portion 201.

IX. CATHETER WITH MANIFOLD ASSEMBLY EMBODIMENT

According to a further embodiment of the present invention, there is provided a manifold for a catheter and in particular a manifold for the catheter depicted in FIGS. 14–15 in which a guide wire port is adapted to automatically both grip a guide wire and provide a fluid seal around the guide wire, and further in which an inflation port is automatically sealed upon disconnection of an inflation device.

As mentioned above, the manifold 208 is located at the proximal end of the balloon catheter 200. The manifold 208 provides for receiving the guide wire 202 and for connecting to a source of inflation fluid for the purpose of inflating the balloon for dilation. Accordingly, the manifold 208 includes a guide wire port 300 and an inflation port 302.

A. Automatic Fluid Seal and Spatial Fixation of Guide Wire

With respect to the guide wire port 300, the manifold 208 provides for several functions. According to an aspect of this embodiment, the catheter portion 201 may be fixed with the guide wire 202 so that catheter portion 201 and guide wire 202 can be advanced intravascularly together in a manner similar to a fixed-wire balloon catheter. For this purpose, the manifold 208 provides for fixing the guide wire 202 with respect to the catheter portion 201. Also, as mentioned above, the catheter portion 201 can be withdrawn from the guide wire 202. Therefore, the manifold 208 also provides for removability of the guide wire 202. Further, because the guide wire 202 and inflation fluid share a common lumen 214 in the shaft 206, the manifold 208 should also provide for a fluid seal so that inflation fluid does not escape through the guide wire port of the manifold. These three features are provided in the embodiment of the manifold disclosed herein as follows.

Referring to FIGS. 17 and 18, there are exploded views of the manifold 208. The manifold 208 includes a manifold body 310 with a main body portion 312 and an inflation port base portion 316 that extends at 90° from the main body portion 312. The manifold body 310 has a main bore 314 extends through the main body 312. The inflation port base portion 316 also has an inflation bore 318 extending therethrough that communicates between the inflation port 302 and the main bore 314. The manifold body 310 and inflation port base portion 316 may be made of a hard plastic material such as polycarbonate.

Located in the main bore 314 directly at the location at which the inflation bore 318 communicates therewith is a manifold body insert 322. The manifold body insert 322 has a generally cylindrical outer shape and is sized to fully occupy a recess 323 in the main body 312 in this region. The manifold body insert 322 has an insert bore 324 extending therethrough having a size at least large enough to accommodate the guide wire 202. The insert bore 324 is tapered so that it is larger distally than at its proximal end for reasons explained below. The manifold body insert 322 includes an annular recess 528 that extends completely around the exterior circumference approximately midway along its length. A manifold insert inflation bore 330 extends from the recess 328 to the insert bore 324. In a preferred embodiment, the manifold body insert 322 is made of a relatively hard plastic material such as polycarbonate.

Immediately proximal of the location in the main bore 314 occupied by the manifold body insert 322, the main bore 314 increases in size forming a shoulder 332. Located in this section of the main bore 314 is a compression seal 336. The compression seal 336 is located directly adjacent the shoulder 332. The compression seal 336 is formed of a soft sealable, elastic material, such as Kraton available from Shell Chemical. The compression seal 336 includes a sealing bore 338 therethrough. The size of the sealing bore 338 through the compression seal 336 is adjustable depending on the compressive forces applied to the compression seal 336. When not under compression, the sealing bore 338 through the compression seal 336 has a diameter of approximately 0.020 inches.

Immediately proximal of the location in the main bore 314 occupied by the compression seal 336 is a collet seat 340. The collet seat 340 has a generally cylindrical outer shape. A collet seat bore 342 extends through the collet seat 340. The collet seat bore 342 is tapered from both its proximal and distal ends 344 and 346 so that a middle portion 348 of the collet seat bore 342 is smaller in diameter than either the proximal or distal ends 344 and 346. The size of the collet seat bore distal end 346 conforms generally to the unstressed diameter of the sealing bore 338. The size of the collet seat smallest diameter at the middle portion 348 is sufficient to accommodate the guide wire 202. In a preferred embodiment, the collet seat 340 is made of a relatively hard plastic material such as Lexan which is available from General Electric.

Immediately proximal of the collet seat 340 and occupying a position partially in the main bore 314 is a collet assembly 352. In a present embodiment, the collet assembly 352 is comprised of a collet body 356 and a collet insert 358. The collet insert 358 is received in a proximal recess 360 of the collet body 356 and snaps into place permanently to form the collet assembly 352. The collet assembly 352 has a collet bore 362 extending therethrough. The collet assembly 352 includes a handle portion 364, a threaded portion 366, and a vise portion 368. The handle portion 364 is defined by an exterior surface of a large diameter proximal portion of the collet assembly 352. When assembled, the handle portion 364 extends proximal of the proximal end of the manifold body 310. The threaded intermediate portion 366 is located immediately distal of the handle portion 364. The threaded intermediate portion 366 is adapted to threadably engage corresponding threads 370 on a proximal portion of the main bore 314 of the manifold body 310. The vise portion 368 is immediately distal of the threaded portion 366. The vise portion 368 includes an elongate cylindrical portion 372 and a tapered distal portion 374. The tapered distal portion 374 of the vise portion 368 is adapted to conform to the tapered proximal portion 344 of the collet seat bore 342. The vise portion 368 is comprised of at least two leaves 378 and 380 separated by a longitudinal slit 382 with the collet bore 262 extending through the leaves 378 and 380. In a preferred embodiment, the collet body 356 and the collet insert 358 are made of a relatively hard plastic material such as Ultem which is available from General Electric Co.

When assembled, the vise portion 368 and threaded portion 366 of the collet assembly 352 extend into the recess 370 of the manifold body 310. The tapered distal portion 374 of the collet assembly is located directly adjacent the proximal tapered portion 344 of the collet seat bore 342. The compression seal 336 is located between the collet seat 340 and the shoulder 332 of the manifold body 310. The manifold body insert 322 is located in a portion of the main bore 314 so that the inflation port passageway 318 is aligned with recess 328 in the insert 322. The collet assembly 352 is rotatably attached to the manifold main body 310 with matable threads 366 and 370 so that the collet assembly 352 can be advanced into and retracted out of the manifold body 310 by rotating the collet assembly 352 relative to the manifold body 310 by means of the handle portion 364. The collet assembly 352 is prevented from being completely withdrawn from the manifold body by a stop 384 on the edge of the collet assembly 352. This stop 384 moves past snap ribs 500 and 501 during assembly and the snap ribs prevent disassembly when the collet handle 364 is turned counterclockwise.

In order to position the guide wire 202 into the catheter portion 201, the guide wire 202, is backloaded into the catheter portion 201, i.e. the proximal end of the guide wire 202 is slid through the distal opening 218 of the catheter portion 201. The guide wire 202 is then advanced back through the catheter portion 201. When the proximal end of the guide wire gets to, the manifold 208, it is received in the main bore 314 passing into the inflation port base portion 316. The proximal end of the guide wire 202 is then received in the insert bore 324. The tapered profile of the insert bore 324 centers the guide wire proximal end as it exits the proximal end of the insert 322 so that it is positioned centrally in the sealing bore 338. The larger distal diameter of the insert bore 324 also provides a larger annular region around the guide wire distally for the conveyance of inflation fluid. The guide wire 202 next extends proximally through the sealing bore 338 of the compression seal 336 and into the distal side 346 of the collet seat 340. As mentioned above, the collet seat bore 342 is tapered so that its proximal and distal ends are larger in size than the middle. The larger distal dimension of the collet seat bore 342 facilitates receiving the guide wire 202 from the compression seal 336. Because the sealing bore 338 is variable in size, the tapered distal portion 346 of the collet seal bore 342 facilitates receiving the guide wire from the compression seal 336 even if it is not exactly aligned centrally. The guide wire next exits the collet seat 340 and enters the collet bore 362 in the collet assembly 352. The guide wire extends through the collet assembly 352 and out the proximal end of the manifold 208. When the guide wire is fully positioned proximally in the catheter portion 201 approximately 10 inches of the proximal end of the guide wire extends proximally out of the manifold 208.

When the catheter system 200 is being positioned, the guide wire 202 and the catheter portion 201 may be advanced together, like a fixed wire catheter, or alternatively, the guide wire 202 may be advanced somewhat ahead of the catheter portion 201. When it is desired to fix the position of the guide wire 202 with respect to the catheter portion 201, the collet assembly 352 is rotated clockwise relative to the manifold body 310 thereby advancing the collet assembly into the manifold body 310. This forces the distal end of the collet assembly into the collet seat 340 and the compression seal 336. The compression seal is compressed between the collet seat 340 and the shoulder 332 of the manifold body 310 causing the compression bore size to be reduced. With a sufficient amount of pressure applied from the collet assembly 352, the compression seal 336 closes down on the guide wire forming an fluid tight seal around the guide wire thereby preventing inflation fluid from leaking out the guide wire port 300.

Advancement of the collet assembly 352 also automatically grips the guide wire 202 in order to fix the position of the guide wire with respect to the manifold 208 (and therefore also the catheter portion 201) so that the guide wire 202 and catheter portion 201 can be handled like a conventional fixed-wire catheter. As mentioned above, rotation of the collet assembly 352 clockwise advances the collet assembly into the manifold body 310 forcing the distal vise portion 368 of the collet assembly 352 into the tapered proximal portion 344 of the collet seat 340. Because the vise portion 368 of the collet assembly has a tapered distal tip 374, moving the collet assembly distally squeezes the tapered distal end portion 374 into the collet seat bore proximal tapered end 344. This has the effect of transferring the axial force from the collet assembly onto the leaves 378 and 380 thereby forcing them together. Because the guide wire occupies an position in the bore 362 between the leaves 378 and 380, this also has the effect of securing the guide wire inside the vise portion 368.

In this manner, the guide wire 202 can be secured in the manifold 208 against axial or rotational movement with respect to the catheter portion 201. Moreover, rotation of the handle portion 364 also automatically compresses the seal 336, as explained above, so that the guide wire 202 can be secured both mechanically and fluidly in the guide wire port 300.

Alternatively, if the physician prefers, it is also possible to position the catheter system 200 by advancing the guide wire 202 independently of the catheter portion 201. In order to operate the catheter portion in this manner, the handle 364 is rotated counterclockwise slightly so that the vise portion 368 no longer secures the guide wire 202 against relative movement with respect the catheter portion 201. Then, the physician can move the guide wire 202 further in advance of the distal end of the catheter portion or rotate the guide wire independently of the catheter portion as needed. When it is desired to fix the guide wire position again, this is readily accomplished by adjustment of the collet assembly handle 364.

The guide wire port 300 on a catheter manifold 208 that provides for automatic fluid sealing around the guide wire and mechanical fixation has particular utility with respect to the embodiment of the catheter system 200 discussed above because the guide wire 201 occupies the same lumen 214 used for inflation fluid. It can be appreciated that the automatic fluid sealing and mechanical fixation guide wire port 300 could also be used on other types of catheters. For example, the embodiment of the guide wire port described above could also be used on an over-the-wire type catheter in which the guide wire occupies a position in a lumen separate from the lumen used for inflation fluid. With such catheters, a fluid seal should be maintained to prevent blood from exiting back through the guide wire lumen. Also, with the over-the-wire type catheter, it may be preferable to mechanically fix the guide wire and catheter to prevent relative movement therebetween. The automatic guide wire port described above could be readily used for such a catheter arrangement.

B. Automatic Sealing of Fluid Port

With respect to the inflation port 302, the manifold 208 provides for several functions. As mentioned above, according to a feature of this embodiment, the catheter portion 201 may be fixed with the guide wire 202 so that catheter portion 201 and guide wire 202 can be advanced intravascularly together similar to a fixed-wire balloon catheter and for this purpose, the manifold 208 provides for fixing the guide wire with respect to the catheter. During this stage of the procedure, the catheter has already been prepped so that it would be preferred to prevent air from entering the inflation lumen. Accordingly, some physicians leave a syringe or inflation device attached to the inflation port to prevent air from entering the inflation lumen. This can be cumbersome and make handling of the catheter more difficult. Stop cock arrangements are sometimes employed, but these can be cumbersome as well.

The manifold 208 in the present embodiment provides for automatically opening the inflation port 302 when a source of inflation fluid is attached and automatically sealing the inflation port when the source of inflation fluid is disconnected. This has the advantage that the physician can readily disconnect the syringe or inflation device during positioning of the catheter without the concern that air may enter the inflation passage.

Referring to FIGS. 17–21, a rotary seal 400 is received into a recess 402 defined by a wall 404 of the inflation port base portion 316 of the manifold body 310. A cap 408 is connected to the inflation port base portion 316 in a manner that provides for limited rotational movement. Specifically, the cap 408 includes skirts 410 and 412. These skirts 410 and 412 will abut a stop 414 located on the inflation port base portion 316 thereby limiting rotational movement of the cap 408 with respect to the inflation port base portion 316 to approximately 90°. In a preferred embodiment, the rotary seal 400 is made of polyethylene and the cap 408 is made of polycarbonate.

Optionally, an O-ring 416 may be located between the cap 408 and the inflation port base portion 316 to provide a fluid tight seal between these two components even during relative rotation. The O-ring may be omitted if a fluid tight seal can be otherwise provided.

The cap 408 includes a top portion having a conventional male Luer fitting 420 to receive a syringe 422 (shown in FIG. 19), inflation device or other apparatus having a conventional male Luer fitting. The cap 408 includes a receiving bore 424 communicating with the Luer fitting. An inner bore 426 extends laterally through an inner wall 428 of the cap 408. The inner wall 428 and an outer wall 430 define a cylindrical recess 432 between them in which the rotary seal 400 and the wall 404 of the inflation port base portion 316 are located. Located in the outer wall 430 of the cap 408 is an outer bore 434. The outer bore 434 is in alignment with the inner bore 426.

As mentioned above, the rotary seal 400 is located in the recess 402 defined by the wall 404 of the inflation port base portion 316. The rotary seal 400 is generally cylindrical in shape as is the wall 404 of the inflation port base portion that defines the recess 402 so that these two pieces fit into the recess 432 in the cap 408. The rotary seal 400 is shaped such that it is fixed against relative rotation with respect to the inflation port base portion 316. The rotary seal 400 includes a venting bore 436 and an inflation bore 438. The venting bore 436 and inflation bore 438 are approximately 90° apart. The venting bore 436 extends from an inside of the rotary seal 400 partially through the rotary seal wall. The inflation bore 438 extends from the inside of the rotary seal wall all the way through the seal wall and also extends downward to a bottom side 440 of the rotary seal 400. The inflation port base portion 316 has a venting bore 442 that extends through the wall 404. When the rotary seal 400 is in position in the inflation port base portion 316, the venting bore 436 of rotary seal is aligned with the venting bore 442 of the inflation port base portion 316 to provide for communication therethrough. However, at the location of the inflation bore 438 of the rotary seal 400, the wall 404 of the inflation port base body 316 is solid and there is no hole through it. Therefore, at the location of the inflation bore 438 of the rotary seal, the only pathway for the inflation fluid is down to the bottom edge 440 of the rotary seal 400. Located in a wall of the inflation port base 316 is the lower bore 318 that communicates from the bottom edge 440 of the rotary seal 400 to the main bore 314.

Figure 21:
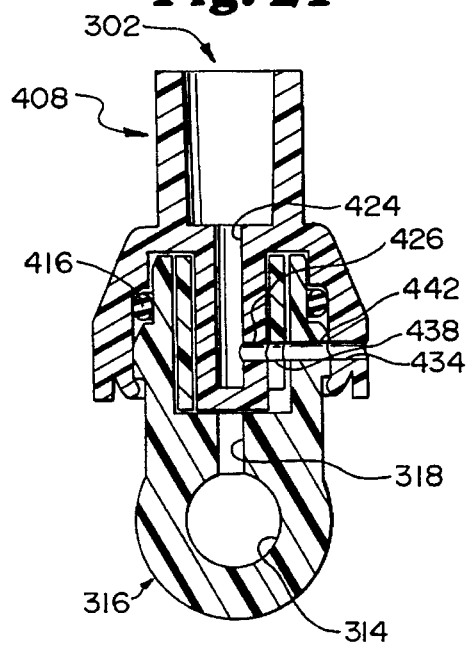
FIG. 21 is a cross sectional view of the inflation port taken along lines 21—21 of FIG. 19 illustrating the inflation port in a venting setting.

When the cap 408 and the inflation port base 316 are aligned as shown in FIG. 21, the venting bore 436 of the rotary seal 400 and the venting bore 442 in the inflation port base portion wall 404 are in alignment with the inner and outer bores 426 and 430 of the cap 408. However, in this position, the cap walls 428 and 430 prevent communication between the receiving bore 424 of the cap and the main bore 314. In this position, the inflation device 422 and the upper portion of the manifold may be vented to remove any air, but the lumen 214 of the catheter shaft is sealed off.

Figure 19:
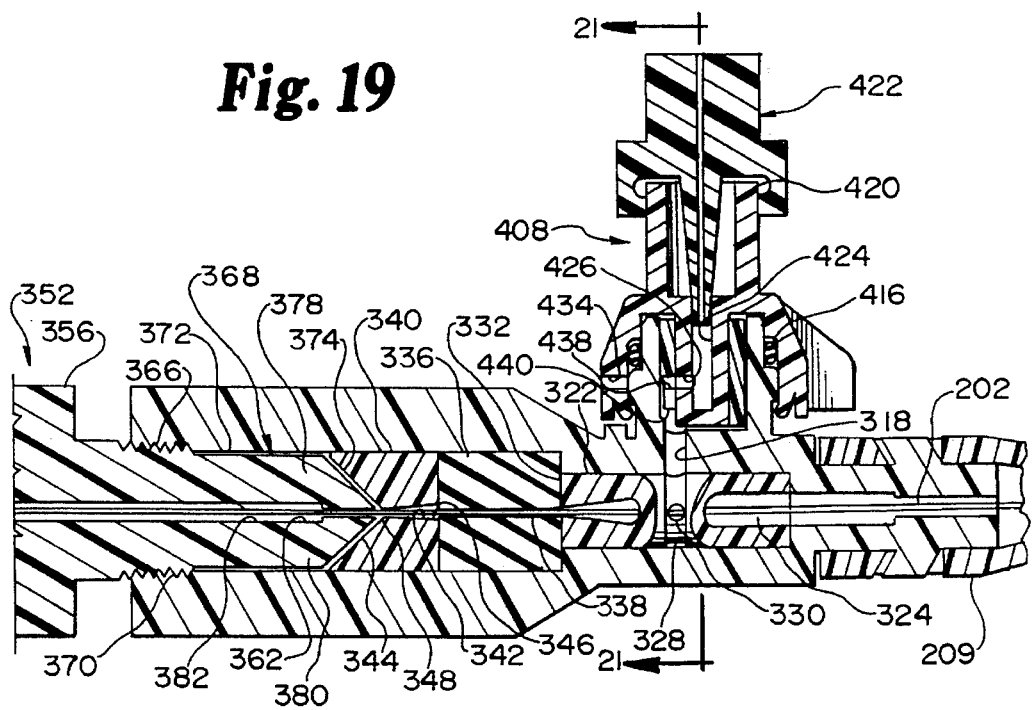
FIG. 19 is a longitudinal sectional view of a portion of manifold assembly of FIG. 17 illustrating the manifold assembly in an inflation setting.
Figure 20:
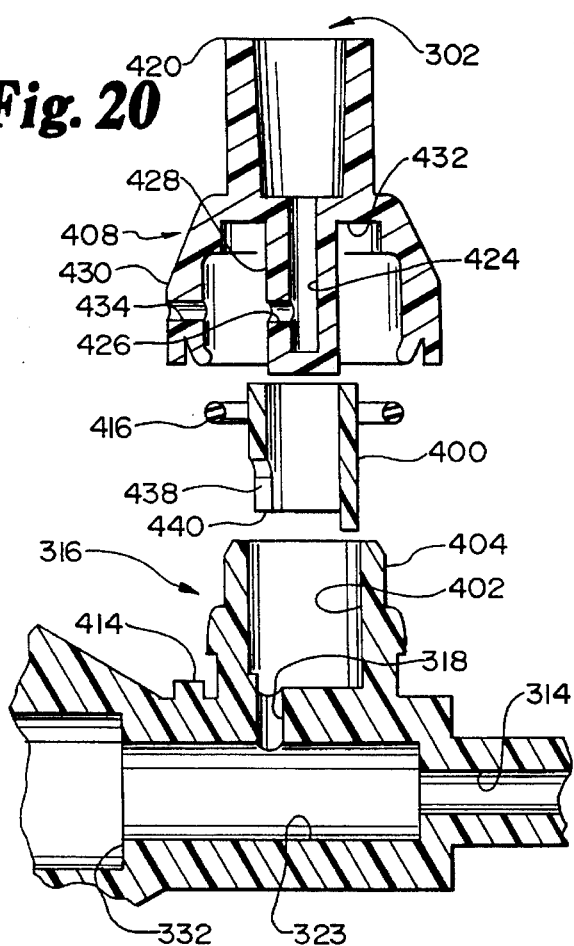
FIG. 20 is an exploded sectional view of the inflation port of FIG. 17.

When the cap 408 and the inflation port base 316 are aligned as shown in FIG. 19 or 20, the inflation bore 438 of the rotary seal 400 is in alignment with the inner bore 426 of the cap. However, since the wall 404 of the inflation port base is directly next to the inflation bore 438 of the rotary seal 400, the only flow passage is down to the bottom 440 of the seal. Thus, fluid communication is provided between the receiving bore 424 and main bore 314 via the inner bore 426 of the cap, the inflation bore 438 of the rotary seal, the lower bore 318 of the inflation port base, and the annular recess 328 and the inflation bore of the insert 322. In this position, the source of inflation fluid 422 is in communication with the main bore 314 and the catheter lumen 214 and therefore, the balloon 204 can be inflated.

The cap 408 and the inflation port base 316 are connected in a manner so that relatively little force is required to rotate the cap 408 relative to the inflation port base 316. Specifically, relatively less force is required to move the cap 408 relative to the manifold body 316 than is required to tighten a syringe or inflation device 422 onto the Luer fitting 420 of the cap. Accordingly, when a syringe or inflation device is positioned onto the female Luer fitting 420 on the cap and the syringe or device is rotated clockwise relative to the manifold body 316, the cap 408 will be made to rotate first thereby moving the cap 408 from the venting position (FIG. 21) to the inflating position (FIG. 19). Then, after the cap is rotated into the inflating position, the skirt 410 abuts the stop 414 preventing further rotation of the cap relative to the manifold body 310. Further rotation applied to the syringe or inflation device 422 will cause relative rotation between the syringe and the cap 408 thereby tightening the Luer fitting to form a fluid tight seal between the syringe and the manifold 208.

Disconnection of the syringe follows in the reverse order. When the syringe 422 is rotated counterclockwise to disconnect it from the manifold 316, the rotational force applied to the syringe will first move the cap 408 from the inflation position to the venting position. When the cap 408 is in the venting position, further counterclockwise force applied to it causes the skirt 412 to abut the stop 414 thereby preventing further relative movement between the cap and inflation port base. Further force applied to the syringe 422 will then cause relative rotation between the syringe and the cap to disconnect the Luer lock. In this manner, the syringe or other inflation device can be connected and disconnected to the manifold 208 and at the same time the inflation passage can be automatically opened and then sealed.

The automatic inflation port sealing feature described above has particular utility when used with the catheter 200. This is because it is important to keep air out of the common lumen 214 shared by the guide wire and inflation fluid. It can be appreciated that the automatic inflation port sealing feature could also be used on other types of catheters, including even those that do not use guide wires. For example, it may be useful to have an automatic fluid sealing port in a catheter used for infusion of dyes or medicines so that the syringe with the dye or medicine fluids can be readily disconnected and the syringe taken off without blood flowing back through the manifold port.

It is intended that the foregoing detailed description be regarded as illustrative rather than limiting and that it is understood that the following claims including all equivalents are intended to define the scope of the invention.

We claim:

1. A balloon catheter system comprising:
   a. an elongate shaft having a proximal and a distal end with a lumen extending therethrough;
   b. an inflatable balloon having a proximal end and a distal end with an interior volume defined therein, said proximal end of said balloon affixed to said elongate shaft proximate the distal end thereof;
   c. means for fluid communication between said interior volume of said balloon and said lumen of said elongate shaft;
   d. a sealing sleeve having a proximal end and a distal end and a lumen extending therethrough, said lumen of said sealing sleeve axially aligned with said lumen of said elongate shaft, wherein said proximal end of said sealing sleeve is distal of said means for fluid communication; and,
   e. a guide wire slidably received through said lumen of said elongate shaft and said lumen of said sealing sleeve, said guide wire including a sleeved portion forming an exterior surface of said guide wire at a location along said guide wire corresponding to the sealing sleeve of said catheter when said guide wire is positioned in said catheter during use, wherein a close tolerance between said sleeved portion of said guide wire and said sealing sleeve forms a seal therebetween during inflation of said inflatable balloon while said guide wire remains slidably received within said lumens.

2. The balloon catheter system of claim 1 wherein said sealing sleeve is a tubular member having sufficient radial strength so that the walls thereof do not collapse onto said guide wire during inflation of said inflatable balloon.

3. The balloon catheter system of claim 2, wherein said sealing sleeve is manufactured from a polymeric material.

4. The balloon catheter system of claim 1, wherein said sleeved portion of said guide wire extends proximally from proximate the distal end thereof.

5. The balloon catheter system of claim 4, wherein said sleeved portion of said guide wire is manufactured from a polymeric material.

6. The balloon catheter system of claim 5, wherein said polymeric material is heat shrunk onto said guide wire.

7. The balloon catheter system of claim 5, wherein said sleeve portion is approximately 6.5 inches in length.

8. The balloon catheter system of claim 1, wherein said proximal end of said sealing sleeve is slidably received within the distal end of said elongate shaft.

9. The balloon catheter system of claim 8, wherein said elongate shaft comprises multiple segments.

10. The balloon catheter system of claim 1, wherein said elongate shaft includes a distal segment which extends distally into the interior volume of said inflatable balloon.

11. The balloon catheter system of claim 10, wherein said means for fluid communication comprise said distal segment having holes through the wall thereof within the interior volume of said inflatable balloon.

12. A balloon catheter system comprising:
   a. an elongate shaft having a proximal and a distal end with a lumen extending therethrough;
   b. an inflatable balloon having a proximal end and a distal end, said proximal end of said balloon affixed to said elongate shaft proximate the distal end thereof and having an interior volume in fluid communication with said lumen of said elongate shaft;
   c. a sealing sleeve having a proximal end and a distal end and a lumen extending therethrough, said sealing sleeve having the distal end of said inflatable balloon affixed thereto and extending proximally through at least a portion of the interior volume of said inflatable balloon, wherein said lumen of said sealing sleeve is axially aligned with said lumen of said elongate shaft; and,
   d. a guide wire slidably received through said lumen of said elongate shaft and said lumen of said sealing sleeve, said guide wire including a sleeved portion forming an exterior surface of said guide wire at a location along said guide wire corresponding to the sealing sleeve of said catheter when said guide wire is positioned in said catheter during use, wherein a close tolerance between said sleeved portion of said guide wire and said sealing sleeve forms a seal therebetween during inflation of said inflatable balloon while said guide wire remains slidably received within said lumen of said elongate shaft and said lumen of said sealing sleeve.

13. The balloon catheter system of claim 12, wherein said sealing sleeve is a tubular member having sufficient radial strength so that the walls thereof do not collapse onto said guide wire during inflation of said inflatable balloon.

14. The balloon catheter system of claim 13, wherein said sealing sleeve is manufactured from a polymeric material.

15. The ball on catheter system of claim 12, wherein said sleeved portion of said guide wire extends proximally from proximate the distal end thereof.

16. The balloon catheter system of claim 15, wherein said sleeved portion of said guide wire is manufactured from a polymeric material.

17. The balloon catheter system of claim 16, wherein said polymeric material is heat shrunk onto said guide wire.

18. The balloon catheter system of claim 16, wherein said sleeve portion is approximately 6.5 inches in length.

19. The balloon catheter system of claim 12, wherein said proximal end of said sealing sleeve is slidably received within the distal end of said elongate shaft.

20. The balloon catheter system of claim 19, wherein said elongate shaft comprises multiple segments.

21. The balloon catheter system of claim 12, wherein said elongate shaft includes a distal segment which extends distally into the interior volume of said inflatable balloon.

22. The balloon catheter system of claim 21, wherein said distal segment includes holes through the wall thereof within the interior volume of said inflatable balloon to provide said fluid communication.

* * * * *